US009222140B2

(12) United States Patent
Tsuboi et al.

(10) Patent No.: US 9,222,140 B2
(45) Date of Patent: Dec. 29, 2015

(54) PRIMERS FOR DETECTING PLASMODIUM

(71) Applicants: EHIME UNIVERSITY, Ehime (JP);
OTSUKA PHARMACEUTICAL CO., LTD., Tokyo (JP)

(72) Inventors: Takafumi Tsuboi, Matsuyama (JP);
Eun-Taek Han, Chuncheon (JP)

(73) Assignees: EHIME UNIVERSITY, Ehime (JP);
OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/571,888

(22) Filed: Dec. 16, 2014

(65) Prior Publication Data

US 2015/0184252 A1 Jul. 2, 2015

Related U.S. Application Data

(62) Division of application No. 13/495,736, filed on Jun. 13, 2012, now Pat. No. 8,936,920, which is a division of application No. 12/602,113, filed as application No. PCT/JP2008/060115 on May 27, 2008, now Pat. No. 8,309,702.

(30) Foreign Application Priority Data

May 28, 2007 (JP) ................................ 2007-140525

(51) Int. Cl.
*C12Q 1/68* (2006.01)
(52) U.S. Cl.
CPC ........ *C12Q 1/6893* (2013.01); *C12Q 2600/158* (2013.01); *C12Q 2600/16* (2013.01)
(58) Field of Classification Search
None
See application file for complete search history.

(56) References Cited

FOREIGN PATENT DOCUMENTS

| JP | 5-227998 A | 9/1993 |
| JP | 6-261758 A | 9/1994 |
| JP | 2003-250564 A | 9/2003 |
| KR | 2003-0032081 A | 4/2003 |
| WO | 00/28082 A1 | 5/2000 |
| WO | 2006/088895 A2 | 8/2006 |

OTHER PUBLICATIONS

Poon, L., et. al., "Sensitive and Inexpensive Molecular Test for Falciparum Malaria: Detecting Plasmodium falciparum DNA Directly from Heat-Treated Blood by Loop-Mediated Isothermal Amplification," Clinical Chemistry, vol. 52, No. 2, (2006), pp. 303-306.
Machouart, M., et. al., "Development of a PCR Assay Followed by Nonradioactive Hybridization Using Oligonucleotides Covalently Bound to CovaLink NH Microwells for Detection of Four Plasmodium Species in Blood Samples from Humans," Journal of Clinical Microbiology, vol. 44, No. 9, pp. 3279-3284, 2006.
Das, A., et. al., Species-specific 18S rRNA gene amplification for the detection of P. falciparum and P. vivax malaria parasites, Molecular and Cellular Probes, Academic Press, London, GB, vol. 9, No. 3, pp. 161-165, 1995.
Rubio, J.M., et. al., "Semi-nested, Multiplex Polymerase Chain Reaction for Detection of Human Malaria Parasites and Evidence of Plasmodium Vivax Infection in Equatorial Guinea", American Journal of Tropical Medicine and Hygiene, vol. 60, No. 2, pp. 183-187, 1999.
Rougemont, M., et. al., "Detection of Four Plasmodium Species in Blood from Humans by 18S rRNA Gene Subunit-Based and Species-Specific Real-Time PCR Assays", Journal of Clinical Microbiology, vol. 43, No. 5, pp. 5636-5643, 2004.
Mangold, K., et. al., "Real-Time PCR Detection and Identification of *Plasmodium* spp.", Journal of Clinical Microbiology, vol. 43, No. 5, pp. 2435-2440, 2005.
Han Eun-Taek et al., "Detection of Four *Plasmodium* Species by Genus- and Species-Specific Loop-Mediated Isothermal Amplification for Clinical Diagnosis", Journal of Clinical Microbiology, vol. 43, No. 5, pp. 2521-2528, 2007.
Notomi, T. et al., "Loop-mediated isothermal amplification of DNA", Nucleic Acids Research, vol. 28, No. 12, e63, 2000.
Database Genbank, Anonymous: "Plasmodium vivax small unit subunit(SSU) rRNA gene," X13926.1, retrieved from NCBI, 1998.
Database Genbank, Anonymous: "P. malaria small subunit ribosomal RNA gene," M54897.1, retrieved from NCBI, 1993.
Database Genbank, Anonymous: "Plasmodium ovale small subunit ribosomal RNA gene, complete sequence" retrieved from NCBI, 1997.
Murty et al., "Database management system for the control of malaria in Arunachal Pradesh, India", Bioinformation, 1(6):194-196, 2006.
Coleman et al., "Developing an Evidence-Based Decision Support System for Rational Insecticide Choice in the Control of African Malaria Vectors", Journal of Medical Entomology, 43(4):663-668, 2006.

*Primary Examiner* — Robert A Zeman
(74) *Attorney, Agent, or Firm* — Sughrue Mion, PLLC

(57) ABSTRACT

The present invention provides an easy and rapid method for detecting/identifying the presence or absence of specific *Plasmodium* parasites and four species of malaria parasites in a human specimen, an anti-malaria measure support system, and a malaria infection-prevention/treatment system, which can contribute to practical diagnosis in a malaria endemic area. According to the present invention, using a genus-specific primer set that can detect four Plasmodium parasites that infect humans at a time, and the primer sets each specific to each of four species of *Plasmodium* parasites (*P. falciparum, P. vivax, P. malariae*, and *P. ovale*), the presence or absence of infection with these parasites can be detected/identified easily and rapidly.

1 Claim, 3 Drawing Sheets

SEQUENCE LISTING

```
<160> NUMBER OF SEQ ID NOS: 47

<210> SEQ ID NO 1
<211> LENGTH: 21
<212> TYPE: DNA
<213> ORGANISM: artificial
<220> FEATURE:
<223> OTHER INFORMATION: Primer for detecting Plasmodium Genus (F3)

<400> SEQUENCE: 1
gtatcaatcg agtttctgac c                                          21

<210> SEQ ID NO 2
<211> LENGTH: 20
<212> TYPE: DNA
<213> ORGANISM: artificial
<220> FEATURE:
<223> OTHER INFORMATION: Primer for detecting Plasmodium Genus (B3c)
```

```
<400> SEQUENCE: 2
cttgtcacta cctctcttct                                              20

<210> SEQ ID NO 3
<211> LENGTH: 45
<212> TYPE: DNA
<213> ORGANISM: artificial
<220> FEATURE:
<223> OTHER INFORMATION: Primer for detecting Plasmodium Genus
      (FIP(F1c-F2))

<400> SEQUENCE: 3
tcgaactcta attccccgtt acctatcagc ttttgatgtt agggt                  45

<210> SEQ ID NO 4
<211> LENGTH: 41
<212> TYPE: DNA
<213> ORGANISM: artificial
<220> FEATURE:
<223> OTHER INFORMATION: Primer for detecting Plasmodium Genus
      (BIP(B1-B2c))

<400> SEQUENCE: 4
cggagaggga gcctgagaaa tagaattggg taatttacgc g                      41

<210> SEQ ID NO 5
<211> LENGTH: 20
<212> TYPE: DNA
<213> ORGANISM: artificial
<220> FEATURE:
<223> OTHER INFORMATION: Primer for detecting Plasmodium Genus (LPF)

<400> SEQUENCE: 5
cgtcatagcc atgttaggcc                                              20

<210> SEQ ID NO 6
<211> LENGTH: 24
<212> TYPE: DNA
<213> ORGANISM: artificial
<220> FEATURE:
<223> OTHER INFORMATION: Primer for detecting Plasmodium Genus (LPB)

<400> SEQUENCE: 6
agctaccaca tctaaggaag gcag                                         24

<210> SEQ ID NO 7
<211> LENGTH: 24
<212> TYPE: DNA
<213> ORGANISM: artificial
<220> FEATURE:
<223> OTHER INFORMATION: Primer for detecting Plasmodium falciparum (F3)

<400> SEQUENCE: 7
tgtaattgga atgataggaa ttta                                         24

<210> SEQ ID NO 8
<211> LENGTH: 23
<212> TYPE: DNA
<213> ORGANISM: artificial
<220> FEATURE:
<223> OTHER INFORMATION: Primer for detecting Plasmodium falciparum
      (B3c)

<400> SEQUENCE: 8
gaaaacctta ttttgaacaa agc                                          23
```

<210> SEQ ID NO 9
<211> LENGTH: 41
<212> TYPE: DNA
<213> ORGANISM: artificial
<220> FEATURE:
<223> OTHER INFORMATION: Primer for detecting Plasmodium falciparum
      (FIP(F1c-F2))

<400> SEQUENCE: 9
agctggaatt accgcggctg ggttcctaga gaaacaattg g                    41

<210> SEQ ID NO 10
<211> LENGTH: 45
<212> TYPE: DNA
<213> ORGANISM: artificial
<220> FEATURE:
<223> OTHER INFORMATION: Primer for detecting Plasmodium falciparum
      (BIP(B1-B2c))

<400> SEQUENCE: 10
tgttgcagtt aaaacgttcg tagcccaaac cagtttaaat gaaac                45

<210> SEQ ID NO 11
<211> LENGTH: 16
<212> TYPE: DNA
<213> ORGANISM: artificial
<220> FEATURE:
<223> OTHER INFORMATION: Primer for detecting Plasmodium falciparum
      (LPF)

<400> SEQUENCE: 11
gcaccagact tgccct                                                16

<210> SEQ ID NO 12
<211> LENGTH: 15
<212> TYPE: DNA
<213> ORGANISM: artificial
<220> FEATURE:
<223> OTHER INFORMATION: Primer for detecting Plasmodium falciparum
      (LPB)

<400> SEQUENCE: 12
ttgaatatta aagaa                                                 15

<210> SEQ ID NO 13
<211> LENGTH: 23
<212> TYPE: DNA
<213> ORGANISM: artificial
<220> FEATURE:
<223> OTHER INFORMATION: Primer for detecting Plasmodium vivax (F3)

<400> SEQUENCE: 13
ggaatgatgg gaatttaaaa cct                                        23

<210> SEQ ID NO 14
<211> LENGTH: 22
<212> TYPE: DNA
<213> ORGANISM: artificial
<220> FEATURE:
<223> OTHER INFORMATION: Primer for detecting Plasmodium vivax (B3c)

<400> SEQUENCE: 14
acgaagtatc agttatgtgg at                                         22

<210> SEQ ID NO 15

```
<211> LENGTH: 42
<212> TYPE: DNA
<213> ORGANISM: artificial
<220> FEATURE:
<223> OTHER INFORMATION: Primer for detecting Plasmodium vivax
      (FIP(F1c-F2))

<400> SEQUENCE: 15
ctattggagc tggaattacc gctcccaaaa ctcaattgga gg                            42

<210> SEQ ID NO 16
<211> LENGTH: 41
<212> TYPE: DNA
<213> ORGANISM: artificial
<220> FEATURE:
<223> OTHER INFORMATION: Primer for detecting Plasmodium vivax
      (BIP(B1-B2c))

<400> SEQUENCE: 16
aattgttgca gttaaaacgc tcgtaagcta gaagcgttgc t                             41

<210> SEQ ID NO 17
<211> LENGTH: 18
<212> TYPE: DNA
<213> ORGANISM: artificial
<220> FEATURE:
<223> OTHER INFORMATION: Primer for detecting Plasmodium vivax (LPF)

<400> SEQUENCE: 17
gctgctggca ccagactt                                                      18

<210> SEQ ID NO 18
<211> LENGTH: 20
<212> TYPE: DNA
<213> ORGANISM: artificial
<220> FEATURE:
<223> OTHER INFORMATION: Primer for detecting Plasmodium vivax (LPB)

<400> SEQUENCE: 18
agttgaattt caaagaatcg                                                    20

<210> SEQ ID NO 19
<211> LENGTH: 18
<212> TYPE: DNA
<213> ORGANISM: artificial
<220> FEATURE:
<223> OTHER INFORMATION: Primer for detecting Plasmodium malariae (F3)

<400> SEQUENCE: 19
caaggccaaa ttttggtt                                                      18

<210> SEQ ID NO 20
<211> LENGTH: 19
<212> TYPE: DNA
<213> ORGANISM: artificial
<220> FEATURE:
<223> OTHER INFORMATION: Primer for detecting Plasmodium malariae (B3c)

<400> SEQUENCE: 20
cggttattct taacgtaca                                                     19

<210> SEQ ID NO 21
<211> LENGTH: 42
<212> TYPE: DNA
<213> ORGANISM: artificial
<220> FEATURE:
<223> OTHER INFORMATION: Primer for detecting Plasmodium malariae
```

(FIP(F1c-F2))

<400> SEQUENCE: 21
tattggagct ggaattaccg cgatgatggg aatttaaaac ct         42

<210> SEQ ID NO 22
<211> LENGTH: 45
<212> TYPE: DNA
<213> ORGANISM: artificial
<220> FEATURE:
<223> OTHER INFORMATION: Primer for detecting Plasmodium malariae
      (BIP(B1-B2c))

<400> SEQUENCE: 22
aattgttgca gttaaaacgc ctatgttata aatatacaaa gcatt      45

<210> SEQ ID NO 23
<211> LENGTH: 19
<212> TYPE: DNA
<213> ORGANISM: artificial
<220> FEATURE:
<223> OTHER INFORMATION: Primer for detecting Plasmodium malariae (LPF)

<400> SEQUENCE: 23
gccctccaat tgccttctg                                   19

<210> SEQ ID NO 24
<211> LENGTH: 24
<212> TYPE: DNA
<213> ORGANISM: artificial
<220> FEATURE:
<223> OTHER INFORMATION: Primer for detecting Plasmodium malariae (LPB)

<400> SEQUENCE: 24
tcgtagttga atttcaagga atca                             24

<210> SEQ ID NO 25
<211> LENGTH: 22
<212> TYPE: DNA
<213> ORGANISM: artificial
<220> FEATURE:
<223> OTHER INFORMATION: Primer for detecting Plasmodium ovale (F3)

<400> SEQUENCE: 25
ggaatgatgg gaatttaaaa cc                               22

<210> SEQ ID NO 26
<211> LENGTH: 21
<212> TYPE: DNA
<213> ORGANISM: artificial
<220> FEATURE:
<223> OTHER INFORMATION: Primer for detecting Plasmodium ovale (B3c)

<400> SEQUENCE: 26
gaatgcaaag aacagatacg t                                21

<210> SEQ ID NO 27
<211> LENGTH: 43
<212> TYPE: DNA
<213> ORGANISM: artificial
<220> FEATURE:
<223> OTHER INFORMATION: Primer for detecting Plasmodium ovale
      (FIP(F1c-F2))

<400> SEQUENCE: 27
tattggagct ggaattaccg cgttcccaaa attcaattgg agg         43

<210> SEQ ID NO 28
<211> LENGTH: 47
<212> TYPE: DNA
<213> ORGANISM: artificial
<220> FEATURE:
<223> OTHER INFORMATION: Primer for detecting Plasmodium ovale
      (BIP(B1-B2c))

<400> SEQUENCE: 28
gttgcagtta aaacgctcgt agtgtattgt ctaagcatct tatagca                47

<210> SEQ ID NO 29
<211> LENGTH: 18
<212> TYPE: DNA
<213> ORGANISM: artificial
<220> FEATURE:
<223> OTHER INFORMATION: Primer for detecting Plasmodium ovale (LPF)

<400> SEQUENCE: 29
tgctggcacc agacttgc                                                18

<210> SEQ ID NO 30
<211> LENGTH: 18
<212> TYPE: DNA
<213> ORGANISM: artificial
<220> FEATURE:
<223> OTHER INFORMATION: Primer for detecting Plasmodium ovale (LPB)

<400> SEQUENCE: 30
tgaatttcaa agaatcaa                                                18

<210> SEQ ID NO 31
<211> LENGTH: 33
<212> TYPE: DNA
<213> ORGANISM: artificial
<220> FEATURE:
<223> OTHER INFORMATION: Primer for detecting Plasmodium vivax (PvFIP-9
      (F1c+F2))

<400> SEQUENCE: 31
cgctattgga gctggaatac tcaattggag ggc                               33

<210> SEQ ID NO 32
<211> LENGTH: 39
<212> TYPE: DNA
<213> ORGANISM: artificial
<220> FEATURE:
<223> OTHER INFORMATION: Primer for detecting Plasmodium vivax (PvBIP-9
      (B1+B2c))

<400> SEQUENCE: 32
aattgttgca gttaaaacga ttaagctaga agcgttgct                         39

<210> SEQ ID NO 33
<211> LENGTH: 16
<212> TYPE: DNA
<213> ORGANISM: artificial
<220> FEATURE:
<223> OTHER INFORMATION: Primer for detecting Plasmodium vivax (PvF3-9)

<400> SEQUENCE: 33
tttaaaacct tcccaa                                                  16

<210> SEQ ID NO 34
<211> LENGTH: 17

```
<212> TYPE: DNA
<213> ORGANISM: artificial
<220> FEATURE:
<223> OTHER INFORMATION: Primer for detecting Plasmodium vivax (PvB3c-9)

<400> SEQUENCE: 34
aagtatcagt tatgtgg                                                  17

<210> SEQ ID NO 35
<211> LENGTH: 15
<212> TYPE: DNA
<213> ORGANISM: artificial
<220> FEATURE:
<223> OTHER INFORMATION: Primer for detecting Plasmodium vivax (PvLPF-9)

<400> SEQUENCE: 35
gctggcacca gactt                                                    15

<210> SEQ ID NO 36
<211> LENGTH: 20
<212> TYPE: DNA
<213> ORGANISM: artificial
<220> FEATURE:
<223> OTHER INFORMATION: Primer for detecting Plasmodium vivax (PvLPB-9)

<400> SEQUENCE: 36
ctcgtagttg aatttcaaag                                               20

<210> SEQ ID NO 37
<211> LENGTH: 32
<212> TYPE: DNA
<213> ORGANISM: artificial
<220> FEATURE:
<223> OTHER INFORMATION: Primer for detecting Plasmodium vivax (PvFIP-7
      (F1c+F2))

<400> SEQUENCE: 37
ctggaattac cgcggctcct tcccaaaact ca                                 32

<210> SEQ ID NO 38
<211> LENGTH: 39
<212> TYPE: DNA
<213> ORGANISM: artificial
<220> FEATURE:
<223> OTHER INFORMATION: Primer for detecting Plasmodium vivax (PvBIP-7
      (B1+B2c))

<400> SEQUENCE: 38
ccaatagcgt atattaaaat tgttgctaga agcgttgct                          39

<210> SEQ ID NO 39
<211> LENGTH: 16
<212> TYPE: DNA
<213> ORGANISM: artificial
<220> FEATURE:
<223> OTHER INFORMATION: Primer for detecting Plasmodium vivax (PvF3-7)

<400> SEQUENCE: 39
tggaatgatg ggaatt                                                   16

<210> SEQ ID NO 40
<211> LENGTH: 18
<212> TYPE: DNA
<213> ORGANISM: artificial
<220> FEATURE:
<223> OTHER INFORMATION: Primer for detecting Plasmodium vivax (PvB3c-7)
```

<400> SEQUENCE: 40
gtatcagtta tgtggatt                                                    18

<210> SEQ ID NO 41
<211> LENGTH: 19
<212> TYPE: DNA
<213> ORGANISM: artificial
<220> FEATURE:
<223> OTHER INFORMATION: Primer for detecting Plasmodium vivax (PvLPF-7)

<400> SEQUENCE: 41
accagacttg ccctccaat                                                   19

<210> SEQ ID NO 42
<211> LENGTH: 23
<212> TYPE: DNA
<213> ORGANISM: artificial
<220> FEATURE:
<223> OTHER INFORMATION: Primer for detecting Plasmodium vivax (PvLPB-7)

<400> SEQUENCE: 42
gcagttaaaa cgctcgtagt tga                                              23

<210> SEQ ID NO 43
<211> LENGTH: 198
<212> TYPE: DNA
<213> ORGANISM: Plasmodium

<400> SEQUENCE: 43
atttagtgtg tgtatcaatc gagtttctga cctatcagct tttgatgtta gggtattggc      60
ctaacatggc tatgacgggt aacggggaat tagagttcga ttccggagag ggagcctgag     120
aaatagctac cacatctaag gaaggcagca ggcgcgtaaa ttacccaatt ctaaagaaga     180
gaggtagtga caagaaat                                                   198

<210> SEQ ID NO 44
<211> LENGTH: 250
<212> TYPE: DNA
<213> ORGANISM: Plasmodium falciparum

<400> SEQUENCE: 44
caatacaata tcgaaaaatg attttgtaat tggaatgata ggaatttaca aggttcctag      60
agaaacaatt ggagggcaag tctggtgcca gcagccgcgg taattccagc tccaatagca     120
tatattaaaa ttgttgcagt taaaacgttc gtagttgaat attaaagaat ccgatgtttc     180
atttaaactg gtttgggaaa accaaatata ttatatattt tgctttgttc aaaataaggt     240
tttctaataa                                                            250

<210> SEQ ID NO 45
<211> LENGTH: 244
<212> TYPE: DNA
<213> ORGANISM: Plasmodium vivax

<400> SEQUENCE: 45
caatacaagg ccaatctggc tttgtaattg gaatgatggg aatttaaaac cttcccaaaa      60
ctcaattgga gggcaagtct ggtgccagca gccgcggtaa ttccagctcc aatagcgtat     120
attaaaattg ttgcagttaa aacgctcgta gttgaatttc aaagaatcga tattttaagc     180
aacgcttcta gcttaatcca cataactgat acttcgtatc gactttgtgc gcattttgct     240
atta                                                                  244

```
<210> SEQ ID NO 46
<211> LENGTH: 266
<212> TYPE: DNA
<213> ORGANISM: Plasmodium malariae

<400> SEQUENCE: 46
caatgcaagg ccaaattttg gttttgcaat tggaatgatg ggaatttaaa accttcccag      60
aaggcaattg gagggcaagt ctggtgccag cagccgcggt aattccagct ccaatagcgt     120
atattaaaat tgttgcagtt aaaacgctcg tagttgaatt tcaaggaatc aatattttaa     180
gtaatgcttt gtatatttat aacatagttg tacgttaaga ataaccgcca aggcttatat     240
tttttctgtt acattttgtt ttatta                                          266

<210> SEQ ID NO 47
<211> LENGTH: 245
<212> TYPE: DNA
<213> ORGANISM: Plasmodium ovale

<400> SEQUENCE: 47
caatacaagg ccatttcatg gttttgtaat tggaatgatg ggaatttaaa accttcccaa      60
aattcaattg gagggcaagt ctggtgccag cagccgcggt aattccagct ccaatagcgt     120
atattaaaat tgttgcagtt aaaacgctcg tagttgaatt tcaaagaatc aatattttaa     180
gtaatacttt tgctataaga tgcttagaca atacaacgta tctgttcttt gcattcctta     240
tgcaa                                                                 245
```

PRIMERS FOR DETECTING PLASMODIUM

CROSS REFERENCE TO RELATED APPLICATIONS

This is a Divisional Application No. 13/495,736 filed Jun. 13, 2012, which is a Divisional of Application No. 12/602,113 filed Feb. 26, 2010 (now U.S. Pat. No. 8,309,702), which is a National Stage of International Application No. PCT/JP2008/060115 filed May 27, 2008, claiming priority based on Japanese Patent Application No. 2007-140525, filed May 28, 2007, the contents of all of which are incorporated herein by reference in their entirety.

TECHNICAL FIELD

The present invention relates to a primer set capable of the rapid and accurate detection/identification of malaria parasites of the genus *Plasmodium* in malaria-endemic areas, a method for detecting and identifying thereof, a detection kit thereof, an anti-malaria measure support system, and a malaria infection-prevention/treatment measure system.

BACKGROUND ART

In many countries where malaria parasites are endemic, the rapid and accurate diagnosis of malaria parasites presents challenges. Of four *Plasmodium* species, *P. falciparum*, which can be fatal, must be identified promptly and distinguished from the other *Plasmodium* species that produce the disease in humans (Moody, A., Clin. Microbiol. Rev. 15 (2002): 66-78).

In addition, most malaria-endemic areas feature infections involving two or more of these species; these mixed infections often go unrecognized or underestimated (Zimmerman, P. A., et al., Trends Parasitol. 20 (2004): 440-447). Failure to detect mixed infection could result in inadequate treatment, and may result in severe disease (Mayxay, M., et al., Trends Parasitol. 20 (2004): 233-240). There is, therefore, an urgent need to develop malaria diagnostic methods that are operable in endemic areas, easy, rapid, highly sensitive and species-specific.

Currently the easy diagnostic method for malaria is microscopic examination of blood smears. Given a high density of parasites, such microscopy has relatively high sensitivity and specificity and provides developmental stage and species determination. However, in endemic areas where parasite density is generally low, this method is labor-intensive, requires well-trained experts, and may result in therapy being delayed.

To improve the speed and precision of malaria diagnosis in regions where standard laboratory diagnosis is not available, researchers have developed rapid diagnostic tests (RDTs) for malaria based on immunoreaction (Moody, A. Clin. Microbiol. Rev. 15 (2002): 66-78; Ndao, M., et al., J. Clin. Microbiol. 42 (2004): 2694-2700). However, the sensitivity varies between products (Murray, C. K., et al., Trop. Med. Int. Health. 8 (2003): 876-883), and a species-specific product is available only for *P. falciparum*. Very long observation times and considerable expertise are required for correct diagnosis by microscopy under several circumstances: when parasitemia is low, during mixed infection, after drug treatment, and during the chronic phase of the infection. Therefore, this situation can lead to false negative results or unreliable species diagnosis (Coleman, R., et al., Thailand. Malar. J. 14 (2006): 121).

Subsequently, molecular-biological methods based on DNA amplification, such as nested PCR and real-time quantitative PCR, were developed for malaria diagnosis. Compared to microscopy, these methods have demonstrated higher sensitivity and greater specificity for mixed infections (Kimura, K., et al., Parasitol. Int. 46 (1997): 91-95; Perandin, F., et al., J. Clin. Microbiol. 42 (2004): 1214-1219; Rougemont, M., et al., J. Clin. Microbiol. 42 (2004): 5636-5643; Singh, B., et al., Am. J. Trop. Med. Hyg. 60 (1999): 687-692; Singh, B., et al., Lancet. 363 (2004): 1017-1024; Snounou, G., et al., Mol. Biochem. Parasitol. 58 (1993): 283-292; Snounou, G., et al., Mol. Biochem. Parasitol. 61 (1993): 315-320). However, the long turnaround time, high cost, and availability only in well-equipped laboratories render this PCR technology inadequate for routine diagnosis in the hospital laboratories and on-site clinics of endemic areas (Hanscheid, T., and Grobusch, M. P., Trends Parasitol. 18 (2002): 395-398).

Regarding malaria detection, Examples 8 and 10 in patent document 1 disclose a method of extracting nucleic acids from blood samples and conducting nested PCR to detect four species of *Plasmodium*. Example 8 discloses each forward primer and the reverse primer sequences, which are different from the primer sequences of the present invention (patent document 1).

Patent documents 2 and 4 Patent Publication disclose methods for detecting one or multiple species of malaria infection based on a solid phase method or nested PCR, in which one or a plurality of multiple types of primers are used to clinically detect *P. falciparum*, *P. vivax*, *P. malariae* or *P. ovale*. However, those primers have different primer sequences to those of the present invention.

Patent documents 3 Patent Publication discloses a method for detecting *P. falciparum* and/or *P. vivax*, in which *P. falciparum* and/or *P. vivax* specific primers are bound to labelor solid supports. However, these specific primer sequences are different from the oligonucleotide sequences of the primer sets of the present invention.

Recently, a novel, easy and highly sensitive technique called loop-mediated isothermal amplification (LAMP) was developed (Notomi, T., et al., Nucleic Acids Res. 28 (2000): e63; WO 2000/28082).

LAMP is a nucleic acid amplification method that relies on auto-cycle strand-displacement DNA synthesis performed by Bst DNA polymerase. The amplified products are stem-loop structures with several repeated sequences of the target, and have multiple loops.

The principal merit of this method is that denaturation of the DNA template is not required, (Nagamine, K., et al., Clin. Chem. 47 (2001): 1742-1743), and thus the LAMP reaction can be conducted under isothermal conditions (ranging from 60 to 65° C.) LAMP requires only one enzyme and four types of primers that recognize six distinct target regions. The method produces a large amount of amplified product, resulting in easier detection, such as detection by visual judgment of the turbidity or fluorescence of the reaction mixture (Mori, Y., et al., Biochem. Biophys. Res. Commun. 289 (2001): 150-154). LAMP in which a fluorescent substance such as fluorescein, fluorescein isothiocyanate (FITC), X-rhodamine (ROX) or the like is used to measure the fluorescence polarization values of the reaction mixture, and LAMP in which SYBR Green 2, a green dye, is used as an intercalator are known (Japanese Unexamined Patent Publication No. 2002-272475, and WO 2002/103053).

Several investigators have reported LAMP methods for the rapid identification of *Plasmodium, Trypanosoma, Babesia, Fusarium, Listeria* and *Legionella*, and have recommended the usefulness of LAMP assay (Ikadai, H., et al., J. Clin. Microbiol. 42 (2004): 2465-2469; Kuboki, N., et al., J. Clin. Microbiol. 41 (2003): 5517-5524; Thekisoe, O., et al., Mol. Biochem. Parasitol. 122 (2002): 223-236; Japanese Unexamined Patent Publication No. 2005-245257, Japanese Unexamined Patent Publication No. 2007-61061, Japanese Unexamined Patent Publication No. 2003-219878 and Poon, L., et al., Clin. Chem. 52 (2006): 303-306).

Poon et al., estimated that the cost of running a LAMP assay is about one tenth that of normal PCR for *P. falciparum* detection (Poon, L., et al., Clin. Chem. 52 (20 06): 303-306). The biggest reduction in cost and time came from simple sample preparation without previous DNA extraction (Iwasaki, M., et al., Genome Lett. 2 (2003): 119-126).

For the preparation of samples, simply heating the infected blood at 99° C. for 10 minutes was enough to prepare a DNA template for LAMP (Poon, L., et al., Clin. Chem. 52 (2006): 303-306). However, to date, LAMP for the detection of malaria parasites in clinical diagnosis has been validated only in acute *P. falciparum* patients (Poon, L., et al., Clin. Chem. 52 (2006): 303-306). Although *P. falciparum* is the most important cause of severe disease, its geographic distribution overlaps with those of *P. vivax, P. malariae* and *P. ovale* infection, and therefore a method allowing the rapid detection and identification of all four species infecting humans would be desirable.

In recent years, in malaria-endemic areas, the development of drug-resistant strains has been a major problem for appropriate malaria treatment. Practicing medical personnel or hospital doctors desire rapid and highly sensitive differentiation methods to obtain information on whether a patient with a fever is infected with a particular malaria parasite or multiple species of malaria parasites, to thereby appropriately treat said malaria patient with a fever.

[Patent document 1] WO2006/88895
[Patent document 2] Japanese Unexamined Patent Publication No. 1994-261758
[Patent document 3] Japanese Unexamined Patent Publication No. 1993-227998
[Patent document 4] Japanese Unexamined Patent Publication No. 2003-250564
[Non-patent document 1] Poon, L., et al., Clin. Chem. 52 (2006): 303-306

DISCLOSURE OF THE INVENTION

Problems to be Solved by the Invention

To solve the above-mentioned problems, the development of easy and rapid methods are desired for the detection and identification of the four species of malaria parasites of the genus *Plasmodium* (particularly, the presence of mixed infections), which are different from known methods such as microscopy or PCR-reaction-mediated methods.

An object of the present invention is to provide a rapid and highly sensitive detection and identification method for clinically detecting and specifying *P. falciparum, P. vivax, P. malariae* or *P. ovale* using LAMP. Further, according to the malaria parasite detection and identification method of the present invention, using blood samples obtained at clinics in malaria-endemic areas, a primer set for detecting the four species of malaria parasites of the genus *Plasmodium*, where the primer set has been evaluated through comparison of microscopy and LAMP; a detection method for the four species of malaria parasites of the genus *Plasmodium* using the primer set; an identification method; and a detection kit are provided.

Therefore, an object of the present invention is to solve the above-mentioned problems, and to provide an easy and rapid detection/identification method for the presence or absence of *Plasmodium* parasites or any one of the 4 specific species of malaria parasites in human specimens, which is capable of contributing to medical care in malaria-endemic areas, and further to provide an anti-malaria measure support system and a malaria infection-prevention/treatment measure system.

Means for Solving the Problems

The present inventors, in aiming to solve such problems, conceived of using a Loop-mediated isothermal amplification (LAMP) method, which is an isothermal gene amplification reaction: (WO 00/28082). However, in general, nucleic acid sequences of malaria parasite genes differ greatly from those of other organisms, being rich in AT content. Therefore, existing primer design software was unable to find optimal primer sets, demanding a repetitive process of trial and error with difficulties in designing each type of primer. Finally, among the many combinations of synthetic primer sets, particularly useful primer sets having both high sensitivity and high specificity were found. Thus, it was found that the use of genus-specific primer sets capable of detecting the four human-infecting species of *Plasmodium* parasites at the same time and primer sets each specific to the four species of parasites (*P. falciparum, P. vivax, P. malariae* and *P. ovale*) allows the easy and rapid detection/identification of the presence or absence of such infections.

It was also found that these results can be effectively used for anti-malaria measure support system and the malaria infection-prevention/treatment measure system can be effectively used.

That is, the present invention can provide the following as described in Items 1 to 27 below.

Item 1. A method for detecting or identifying infection with the genus *Plasmodium* and/or one or more of *Plasmodium falciparum, Plasmodium vivax, Plasmodium malariae*, and *Plasmodium ovale* in a specimen; the method comprising the following steps (a) to (c):
a) extracting DNA from the specimen;
b) amplifying a particular region of a *Plasmodium* 18S rRNA gene sequence by reacting the DNA extracted in the step (a) in a reaction mixture containing a strand displacement DNA polymerase and a sequence-specific primer set; and
c) detecting or identifying the presence or absence of an amplified product of the genus *Plasmodium* and/or one or more of *Plasmodium falciparum, Plasmodium vivax, Plasmodium malariae*, and *Plasmodium ovale*, amplified in the step (b);

the sequence-specific primer set being an oligonucleotide set containing nucleic acid sequences represented by SEQ ID NOs: 1 to 6 for amplifying a particular region of a *Plasmodium* 18S rRNA gene sequence; and/or one or more of a primer set comprising an oligonucleotide set containing nucleic acid sequences represented by SEQ ID NOs: 7 to 12 for amplifying a particular region of a *Plasmodium falciparum* 18S rRNA gene sequence, a primer set comprising an oligonucleotide set containing nucleic acid sequences represented by SEQ ID NOs: 13 to 18, SEQ ID NOs: 31 to 36, or SEQ ID NOs: 37 to 42 for amplifying a particular region of a *Plasmodium vivax* 18S rRNA gene sequence, a primer set comprising an oligonucleotide set containing nucleic acid sequences represented by SEQ ID NOs: 19 to 24 for amplifying a particular region of a *Plasmodium malariae* 18S rRNA gene sequence, and a primer set comprising an oligonucleotide set containing nucleic acid sequences represented by SEQ ID NOs: 25 to 30 for amplifying a particular region of a *Plasmodium ovale* 18S rRNA gene sequence.

Item 2. A detection or identification method according to Item 1, wherein the DNA extraction from the specimen is carried out by boiling the specimen containing the DNA, and performing centrifugation.

Item 3. A detection or identification method according to Item 2, wherein the boiling time is from several minutes to ten and several minutes.

Item 4. A detection or identification method according to any one of Items 1 to 3, wherein, in the step (b) of amplifying a particular region of a *Plasmodium* 18S rRNA gene sequence, the DNA amplification reaction is performed at about 60° C. for about 1 hour using a constant-temperature water bath or an amplifier specially designed for LAMP.

Item 5. A detection or identification method according to any one of Items 1 to 4, wherein, in the step (C), the presence or absence of an amplification product of the genus *Plasmodium*, and/or one or more of *Plasmodium falciparum, Plasmodium vivax, Plasmodium malariae*, and *Plasmodium ovale* is detected or identified using visual observation or a real-time turbidimeter.

Item 6. A detection or identification method according to any one of Items 1 to 5, which is performed in a malaria endemic area.

Item 7. A detection or identification method according to any one of Items 1 to 6, wherein infections with the genus *Plasmodium* and/or one or more of *Plasmodium falciparum, Plasmodium vivax, Plasmodium malariae*, and *Plasmodium ovale* are detected or identified simultaneously or separately.

Item 8. A detection or identification method according to any one of Items 1 to 6, wherein infection with the genus *Plasmodium* is detected or identified using, as the sequence-specific primer set, a primer set comprising an oligonucleotide set containing nucleic acid sequences represented by SEQ ID NOs: 1 to 6 for amplifying a particular region of a *Plasmodium* 18S rRNA gene sequence.

Item 9. A detection or identification method according to any one of Items 1 to 6, wherein infection with *Plasmodium vivax* is detected or identified using, as the sequence-specific primer set, a primer set for detecting *Plasmodium vivax* that comprises an oligonucleotide set containing nucleic acid sequences represented by SEQ ID NOs: 13 to 18, SEQ ID Nos: 31 to 36, or SEQ ID Nos: 37 to 42 and that is capable of amplifying a particular region of a *Plasmodium vivax* 18S rRNA gene sequence.

Item 10. A detection or identification method according to any one of Items 1 to 6, wherein infection with *Plasmodium malariae* is detected or identified using, as the sequence-specific primer set, a primer set for detecting *Plasmodium malariae* that comprises an oligonucleotide set containing nucleic acid sequences represented by SEQ ID NOs: 19 to 24 and that is capable of amplifying a particular region of a *Plasmodium malariae* 18S rRNA gene sequence.

Item 11. A detection or identification method according to any one of Items 1 to 6, wherein infection with *Plasmodium ovale* is detected or identified using, as the sequence-specific primer set, a primer set for *Plasmodium ovale* that comprises an oligonucleotide set containing nucleic acid sequences represented by SEQ ID NOs: 25 to 30 and that is capable of amplifying a particular region of a *Plasmodium ovale* 18S rRNA gene sequence.

Item 12. A primer set for detecting the genus *Plasmodium*, comprising an oligonucleotide set containing nucleic acid sequences represented by SEQ ID NOs: 1 to 6, the primer set being capable of amplifying a particular region of a *Plasmodium* 18S rRNA gene sequence.

Item 13. A primer set for detecting *Plasmodium vivax*, comprising an oligonucleotide set containing nucleic acid sequences represented by SEQ ID NOs: 13 to 18, SEQ ID NOs: 31 to 36, or SEQ ID NOs: 37 to 42, the primer set being capable of amplifying a particular region of a *Plasmodium vivax* 18S rRNA gene sequence.

Item 14. A primer set for detecting *Plasmodium malariae*, comprising an oligonucleotide set containing nucleic acid sequences represented by SEQ ID NOs: 19 to 24, the primer set being capable of amplifying a particular region of a *Plasmodium malariae* 18S rRNA gene sequence.

Item 15. A primer set for detecting *Plasmodium ovale*, comprising an oligonucleotide set containing nucleic acid sequences represented by SEQ ID NOs: 25 to 30, the primer set being capable of detecting a particular region of a *Plasmodium ovale* 18S rRNA gene sequence.

Item 16. A primer set for detecting the genus *Plasmodium* and/or any one of *P. falciparum, P. vivax, P. malariae*, and *P. ovale*, comprising an oligonucleotide primer set containing nucleic acid sequences selected from those defined in Items 12 to 15 and nucleic acid sequences represented by SEQ ID NOs: 7 to 12, the primer set being capable of amplifying particular regions of 18S rRNA gene sequences of the genus *Plasmodium* and various species of *Plasmodium* including a particular region of a *Plasmodium falciparum* 18S rRNA gene sequence.

Item 17. A detection kit for the genus *Plasmodium* and/or any one of *P. falciparum, P. vivax, P. malariae*, and *P. ovale*; comprising at least a primer set selected from the primer sets defined in Items 12 to 16, a strand displacement DNA polymerase, dNTPs and a reaction buffer.

Item 18. A detection kit according to Item 17, wherein the detection kit detects the genus *Plasmodium* and/or *P. falciparum, P. vivax, P. malariae*, and *P. ovale*, simultaneously or separately.

Item 19. An anti-malaria measure support system comprising:

means for inputting and storing malaria-infected patient information including the number positive for the genus *Plasmodium* parasites that cause malaria in a malaria endemic area, and the carrier rate in the area;

a malaria infection-prevention public health measure guide database that specifies public health measures for the malaria endemic area based on the malaria-infected patient information, into which database public health measure selection information for a malaria parasite-infected area to be inputted together with the measure priority indicating which of the public health measures should be given priority in selection has been inputted;

a public health measure extraction section that extracts public health measures for the malaria-infected endemic area and the priority thereof from the malaria infection-prevention public health measure guide database, according to malaria-infected patient information about malaria parasites in a subject; and a public health measure display section that displays the public health measures extracted in the public health measure extraction section, together with the priority thereof.

Item 20. An anti-malaria measure support system according to Item 19, wherein the malaria-infected patient information about malaria parasites in the malaria endemic area is obtained by identifying the presence or absence of infection with the genus *Plasmodium* using a detection or identification method according to Item 1 and/or a primer set according to Item 12, or the *Plasmodium* detection kit according to Item 17.

Item 21. An anti-malaria measure support system comprising:

means for inputting and storing malaria parasite therapeutic agent information for specifying a malaria therapeutic agent that acts on infection with one or a plurality of four species of malaria parasites;

patient information input means for inputting and storing patient information including information about the pathogen of malaria infection in a patient with a fever in a malaria endemic area;

patient information input means for inputting and storing patient information including information about the pathogen of malaria infection in a patient with a fever in a malaria non-endemic area;

a treatment guide database into which, according to indices of efficacy against malaria parasites detected in a subject, malaria parasite therapeutic agent selection information to be inputted together with a priority that indicates which malaria therapeutic agent should be given priority in selection for use against the malaria parasites;

a malaria therapeutic agent extraction section that extracts, according to the information about the pathogen of malaria infection in the subject, malaria therapeutic agents to be administered and the priority thereof, from the treatment guide database; and a malaria therapeutic agent display section that displays the malaria therapeutic agents extracted in the above malaria therapeutic agent extraction section, together with the priority thereof.

Item 22. An anti-malaria measure support system according to Item 21, wherein the information about the pathogen of malaria infection in a patient with a fever is obtained by identifying infection with one or a plurality of four species of malaria parasites using a detection or identification method according to any one of Items 1 to 11 and/or a primer set according to any one of Items 12 to 16, or a detection kit according to Item 17 or 18.

Item 23. An anti-malaria measure support system in which a public health measure relating to an anti-malaria measure and a malaria parasite treatment measure relating to an anti-malaria measure are carried out in combination;

the public health measure comprising:

means for inputting and storing malaria-infected patient information including the number positive for the genus *Plasmodium* that causes malaria in a malaria endemic area, and the carrier rate in the area;

a malaria infection-prevention public health measure guide database that specifies public health measures for the malaria endemic area based on the malaria-infected patient information, into which database public health measure selection information for a malaria parasite-infected area to be inputted together with a priority of measures that indicates which of the public health measures should be given priority in selection has been inputted;

a public health measure extraction section that extracts public health measures for the malaria-infected endemic area and the priority thereof, from the malaria infection-prevention public health measure guide database according to malaria-infected patient information about malaria parasites in the subject; and a public health measure display section that displays the public health measures extracted in the public health measure extraction section, together with the priority thereof; and the malaria parasite treatment measure comprising:

means for inputting and storing malaria parasite therapeutic agent information for specifying a malaria therapeutic agent that acts on infection with one or a plurality of four species of malaria parasites;

patient information input means for inputting and storing patient information including information about the pathogen of malaria infection in a patient with a fever in the malaria endemic area;

patient information input means for inputting and storing patient information including information about the pathogen of malaria infection in a patient with a fever in a malaria non-endemic area;

a treatment guide database into which, according to indices of efficacy against malaria parasites detected in a specimen, malaria parasite therapeutic agent selection information to be inputted together with a priority that indicates which malaria therapeutic agent should be given priority in selection for use against the malaria parasites;

a malaria therapeutic agent extraction section that extracts, according to the information about the pathogen of malaria infection in the subject, malaria therapeutic agents to be administered and the priority thereof, from the treatment guide database; and a malaria therapeutic agent display section that displays the malaria therapeutic agents extracted in the above malaria therapeutic agent extraction section, together with the priority thereof.

Item 24. An anti-malaria measure support system according to Item 23, wherein the malaria-infected patient information about malaria parasites in the malaria endemic area is obtained by identifying the presence or absence of infection with the genus *Plasmodium* using a detection or identification method according to Item 1 and/or a primer set according to Item 12, or the genus *Plasmodium* detection kit according to Item 17 or 18; and/or information about the pathogen of malaria infection in a patient with a fever is obtained by identifying infection with one or a plurality of four species of malaria parasites using a detection or identification method according to any one of Items 1 to 11 and/or a primer set according to Item 16, or a *Plasmodium* species detection kit according to Item 17 or 18.

Item 25. A malaria infection-prevention measure system for persons who plan to travel to a malaria endemic area, the system comprising:

means for obtaining the state of the implementation of public health measures in the malaria endemic area, information about the pathogens of malaria infection in the endemic area, and the state of the treatment of infected patients, from the anti-malaria measure support system according to Item 23;

means for selecting a malaria prophylactic/therapeutic agent from a malaria parasite treatment guide database; and means for administering the selected agent before travel.

Item 26. A malaria infection-prevention/treatment measure system for returnees from a malaria endemic area, the system comprising:

means for obtaining the state of the implementation of public health measures in the malaria endemic area, information about the pathogens of malaria infection in the endemic area, and the state of the treatment of infected patients;

means for selecting a malaria prophylactic/therapeutic agent from a malaria parasite treatment guide database; and means for administering the selected agent after returning from the malaria endemic area, according to Item 23.

Item 27. A malaria infection-prevention/treatment measure system according to Item 26, wherein, when a returnee from the malaria endemic area has a fever, identification of *Plasmodium falciparum, Plasmodium vivax, Plasmodium malariae,* or *Plasmodium ovale* is performed to select and administer a malaria therapeutic agent that should be given priority in selection.

Use of one of the primers or primer set of the above Items (1) to (5) for LAMP allows the annealing of a particular region of the genus *Plasmodium* 18S rRNA gene, a *P. falciparum* 18S rRNA gene, a *P. vivax* 18S rRNA gene, a *P. malariae* 18S rRNA gene or a *P. ovale* 18S rRNA gene. Amplifying this under the amplification conditions of the LAMP method allows amplification of a specific gene region. The presence or absence of such an amplification product is analyzed by electrophoresis or an easy detection method. In such a method, infections by the specific genus *Plasmodium* and each of the four species of malaria parasites can be simultaneously or separately detected and differentiated.

When the detection method of the present invention is used for specific specimens (for example, human blood), DNA samples can be isolated from the specimens, with these DNA samples, any one of the primer sets of Item (1) to Item (5) were reacted for amplification, thereby confirming the presence or absence of any amplified DNA products. In such a way, any of the genus *Plasmodium* or the four species of malaria parasites: *P. falciparum, P. vivax, P. malariae* or *P. ovale* can be detected simultaneously or separately.

Effects of the Invention

The present invention allows the use of a primer set for LAMP, wherein the primer set comprises an oligonucleotide set containing the nucleic acid sequences of SEQ ID NOs: 1 to 6, 7 to 12, 13 to 18 (31 to 36 or 37 to 42), 19 to 24 or 25 to 30; and allows the simultaneous or separate amplification of a common region of the genus *Plasmodium* 18S rRNA genes, or a particular region of the 18S rRNA genes of each of the four species of human malaria parasites: *P. falciparum, P. vivax, P. malariae* or *P. ovale;* thereby allowing simultaneous or separate detection or differentiation of the presence or absence of any human malaria parasite infection or one of the four species of human malaria parasites.

The method for detecting or differentiating the presence or absence of malaria parasite infection or one of the four species of human malaria parasites of the present invention comprises: amplifying DNA samples obtained from specimens by LAMP (isothermal gene amplification) using a primer set comprising the oligonucleotide set containing the nucleic acid sequences of SEQ ID NOs: 1 to 6, 7 to 12, 13 to 18 (31 to 36 or 37 to 42), 19 to 24 or 25 to 30; and analyzing the presence or absence of any amplification products. Such a detection or differentiation method allows easy, rapid and reliable detection or differentiation of the presence or absence of any malaria parasite infections, or one of the four species of malaria parasites: *P. falciparum, P. vivax, P. malariae* or *P. ovale* simultaneously or separately. The present invention also provides a kit for the simultaneous or separate detection or identification of such human malaria parasites or the four species of malaria parasites.

The development of drug-resistant strains has become a major issue for appropriately treating malaria. The method for simultaneously differentiating the four species of malaria parasites: *P. falciparum, P. vivax, P. malariae* and *P. ovale* of the present invention provides, in malaria-endemic regions, practicing medical personnel or hospital doctors with rapid and highly sensitive information on whether a patient with a fever is infected with a particular malaria parasite or multiple malaria parasites, allowing rapid and appropriate treatment for a malaria patient with a fever.

The use of the genus *Plasmodium* or the four species of malaria parasite detection/identification method of the present invention makes it possible to monitor the therapeutic effects of malaria therapeutic agent administration to malaria-infected patients.

According to the anti-malaria measure support system of the present invention, clinical practitioners and hospital doctors can check information about the pathogen of malaria infection in a patient with a fever against the malaria therapeutic agent guide database in a PC or via a cellular phone to have a conventional software to operate, thereby obtaining a display of which malaria therapeutic agent should be given priority in selection, or which malaria therapeutic agents should be used in combination.

Using the malaria infection-prevention measure system of the present invention, it is possible for a person who plan to travel to a malaria endemic area to know beforehand the malaria infections that are endemic in the area and the state of appearance of drug-resistant strains. Thus, to prevent malaria infection, the person can take, before travel, a preferable malaria therapeutic agent to be given priority in selection for use against the malaria infections that are endemic in the area, so that even if the person should be infected with malaria, symptoms due to malaria infection, such as a fever, can be reduced at an early stage and serious conditions can be prevented, making it possible to exterminate malaria parasites from the person's blood at an early stage.

BEST MODE FOR CARRYING OUT THE INVENTION

Figure 1:
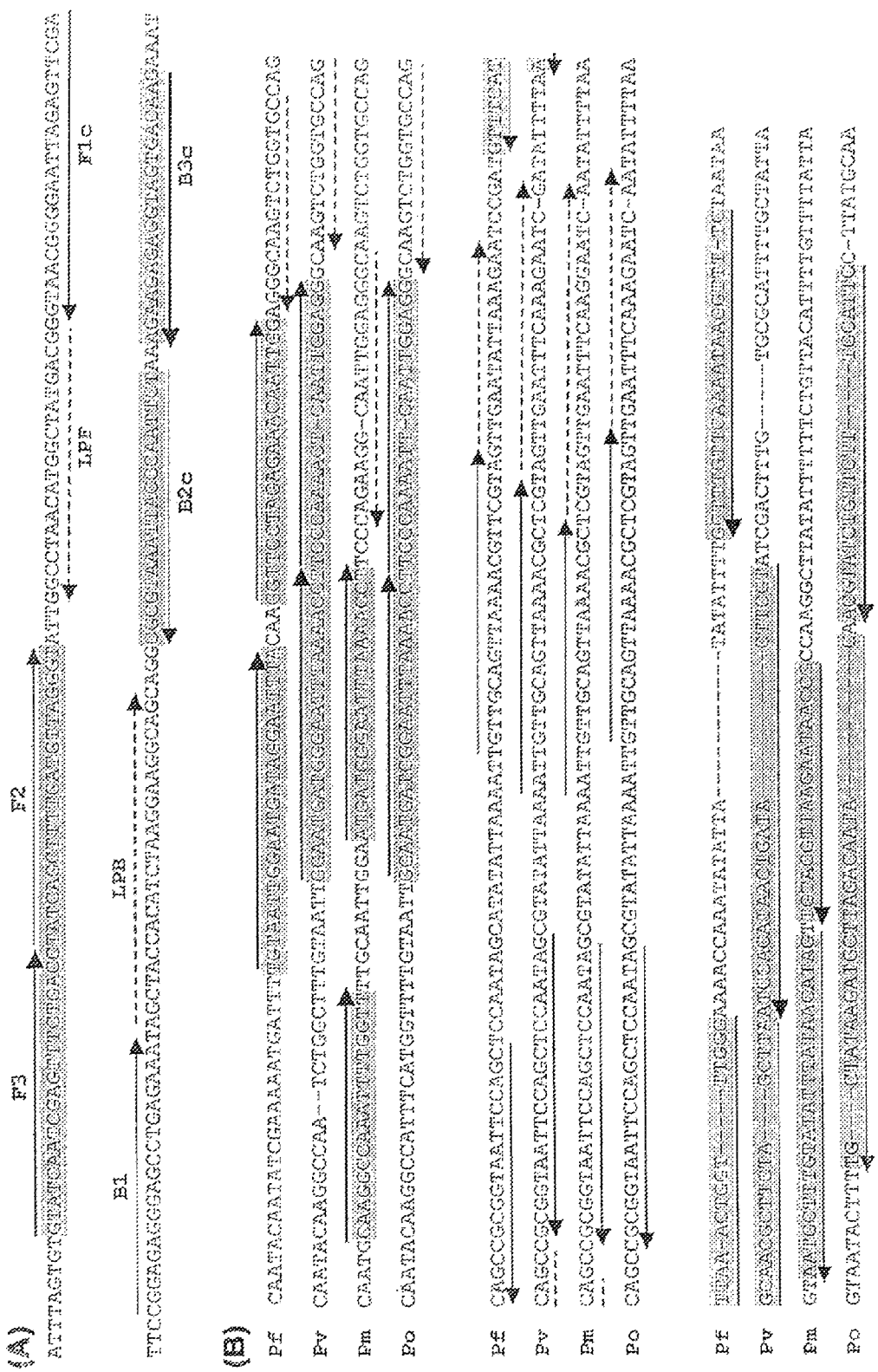
FIG. 1 shows the locations of LAMP targets and priming sites for *Plasmodium* genus (A) and four *Plasmodium* species (B), and the 18S rRNA gene nucleotide sequences. (A) The locations of the priming sites by the *Plasmodium* genus-specific primer set in the reference sequence (GenBank Accession No. M19173.1) are indicated by arrows. (B) Partial sequence alignment of the 18S rRNA genes of four human malaria parasites, *P. falciparum* (Pf; GenBank Accession No. M19173.1), *P. vivax* (Pv; GenBank Accession no. U03079), *P. malariae* (Pm; GenBank Accession No. M54897), and *P. ovale* (Po; GenBank Accession No. L48986), along with the species-specific primer annealing sites.
Figure 2:
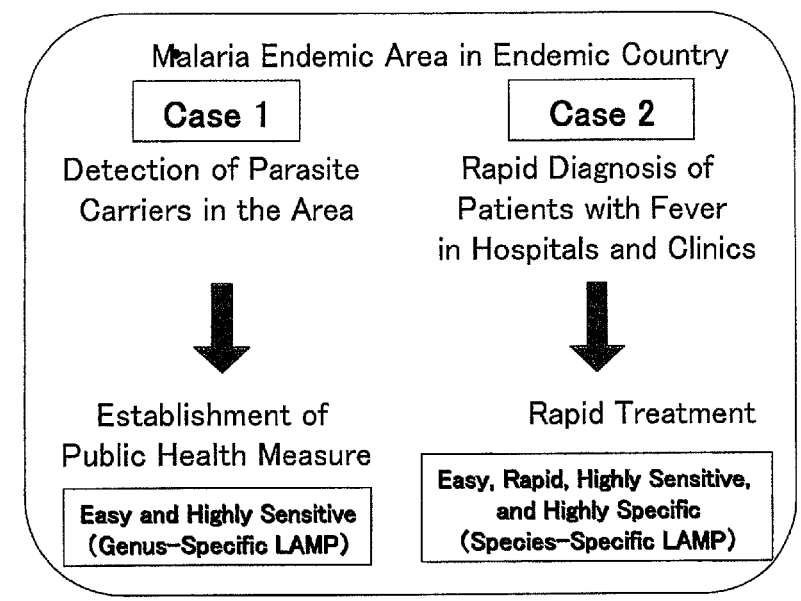
FIG. 2 is a schematic diagram of the anti-malaria measure support system using LAMP.
Figure 2:
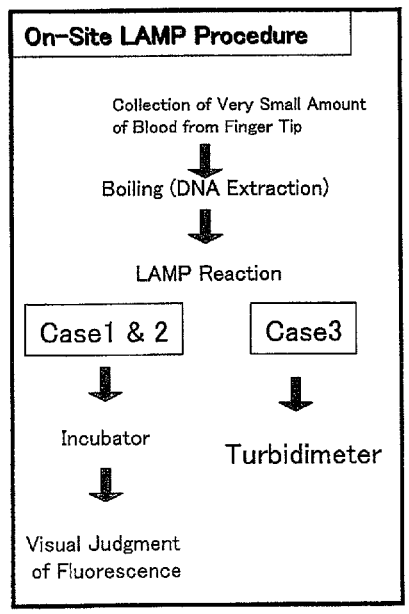
Figure 2:
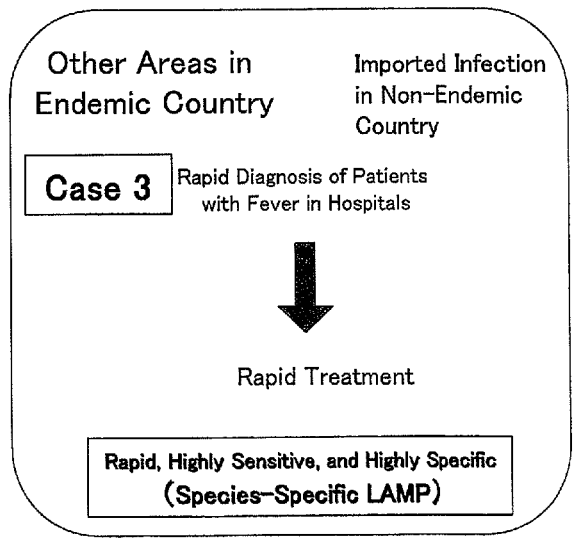

Preferred embodiments of the present invention are explained in detail below.

The present invention is an easy and highly reliable detection system for routine malaria parasite screening, both at hospitals and laboratories, or at malaria clinics in endemic areas. For example, the genus *Plasmodium* or any one of the four species of malaria parasites: *P. falciparum, P. vivax, P. malariae* or *P. ovale* when present in human blood samples are determined by an isothermal gene amplification method that employs LAMP using oligonucleotide primers specific to the genus *Plasmodium* and each one of the four species of malaria parasites. Specifically, the invention is based on a method comprising the steps of targeting a particular region of the genus specific *Plasmodium* 18S rRNA gene sequence, the *P. falciparum* 18S rRNA gene sequence, *P. vivax* 18S rRNA gene sequence, *P. malariae* 18S rRNA gene sequence, or *P. ovale* 18S rRNA gene sequence; amplifying the particular region of the *Plasmodium* 18S rRNA gene sequence, the *P. falciparum* 18S rRNA gene sequence, *P. vivax* 18S rRNA gene sequence, *P. malariae* 18S rRNA gene sequence or *P. ovale* 18S rRNA gene sequence using the primer set of Item 16; and analyzing the presence or absence of any amplification products.

The detection/identification method of the present invention can be applied to malaria parasites present in human blood that is infected with malaria parasites.

As used herein, the term "specimen" may include the genus *Plasmodium* or one of the four specific species of malaria parasites: *P. falciparum*, *P. vivax*, *P. malariae* or *P. ovale*, implying human blood samples to be targeted by the detection/identification method of the present invention. As used herein, the term "detection" implies, for example, determining whether malaria parasites present in a blood sample are malaria parasites of a specific *Plasmodium* species, and is sometimes used as a synonym for determination.

As used herein, the term "identification" sometimes implies distinguishing between specific *Plasmodium* species such as *P. falciparum*, *P. vivax*, *P. malariae* or *P. ovale* and the other *Plasmodium* species; and detecting simultaneously or separately; in specimens where at least one species of *Plasmodium* species is present. However, the term "identification" generally implies identifying a particular malaria parasite to be detected amongst multiple malaria parasites. Hence, the term "identification" includes the detection of single malaria parasite infections and multiple malaria parasite infections.

The LAMP method used in the present invention is a gene amplification method in which, unlike PCR, thermoregulation (thermal cycle) is not required in the amplification steps, one kind of DNA polymerase is used, and genes are amplified at a constant temperature (isothermal temperature) (WO 2000/28082 and Notomi, T., et al., Nucleic Acids Res. 28 (2000): e63). The above DNA polymerase may be any template-dependent nucleic acid synthetic enzyme that processes strand displacement activity. Such enzymes include Bst DNA polymerase (Large Fragment), Bca (exo-) DNA polymerase, the Klenow fragment of Escherichia coli DNA polymerase I, Vent (Exo-) DNA polymerase (Vent DNA polymerase without exonuclease activity), DeepVent (Exo-) DNA polymerase (DeepVent DNA polymerase without exonuclease), KOD DNA polymerase and the like.

Bst DNA polymerase (Large Fragment) is preferably used. When this enzyme is used, the reaction is preferably performed around at 65° C., which is an optimum temperature for the enzyme reaction.

An amplified product of the LAMP method can be detected by known techniques. For example, it can be detected using a labeled oligonucleotide that specifically recognizes the amplified gene sequence; or the reaction mixture can be directly subjected to agarose electrophoresis after completion of the reaction for easy detection. The LAMP method produces a ladder of multiple bands having different base lengths.

Furthermore, the white suspension caused by magnesium pyrophosphate accumulation as a by-product of amplification can be detected by the naked eye or with a turbidimeter (Mori, Y., et al. Biochem. Biophys. Res. Commun. 289 (2001): 150-154).

Alternatively, amplification can be simply inspected with the naked eye using SYBR Green I (product of Applied Biosystems), which turns green in the presence of amplified DNA. However, SYBR Green I results were consistent with those deduced from a real-time turbidimeter (Parida, M., et al., J. Clin. Microbiol. 43 (2005): 2895-2903 and Japanese Unexamined Patent Publication No. 2001-242169). Since the turbidity assay can be carried out in a closed system, the risk of contamination is lower than that for agarose gel electrophoresis. This is an additional merit of LAMP in clinical use (Enosawa, M., et al. J. Clin. Microbiol. 41 (2003): 4359-4365; Seki, M., et al., J. Clin. Microbiol. 43 (2005): 1581-1586; Poon, L., et al., Clin. Chem. 52 (2006): 303-306).

Thus, LAMP diagnosis, in principle, does not require expensive reagents for DNA extraction, a turbidimeter, a thermal cycler, or a skilled technician). The template can be prepared by direct heat-treatment of blood samples, without time-consuming and expensive DNA extractions using a commercial kit.

For example, in the field in malaria-endemic areas, only boiling and separating a very small amount of blood from a subject's fingertip allows the preparation of a desired DNA sample enough for the LAMP reaction.

Moreover, LAMP requires only a simple incubator, such as a heat block or a water-bath that provides a constant 60° C., which makes it more economical and practical than nested PCR or real-time PCR.

A genus specific primer set common to the four species of human malaria parasite 18S rRNA genes, and each specific primer set of the present invention for the *P. vivax* 18S rRNA gene, *P. malariae* 18S rRNA gene, and *P. ovale* 18S rRNA gene, target particular regions of each 18S rRNA gene. The primer sets are designed to have a total of 4 kinds of primer as a set, in which two are loop forming 2 kinds of inner primers: (FIP(F1c-F2) and BIP(B1-B2c)), and the other two are 2 kinds of outer primers (F3, B3c). Particular regions of each amplified gene range between about 70 to 500 base pair length.

The inner primers amplify the nucleic acid sequence of the target region, and are characterized by including: (a) as a first segment, a nucleic acid sequence that anneals the target gene and functions as a primer; and (b) as a second segment, a nucleic acid sequence that is complementarily to the 3' nucleic acid sequence of the first segment, and positions at the 5' side of the first segment.

Further, use of loop primers (LPB, LPF) having a complementary sequence to the single strand portion of the dumbbell structure's 5' terminus loop, where the dumbbell structure functions as the origin of the amplification reaction, can increase the number of origins in DNA synthesis. Therefore, use of loop primers can increase amplification efficacy, and shorten the time required for amplification to about one third to a half. Outer primers recognize the 3' terminus nucleic acid sequence of the target region, and have a nucleic acid sequence functioning as the origin of the synthesis.

The inventors attempted to design each inner primer ((FIP (F1c-F2), BIP(B1-B2c)), outer primer (F3, B3c) and loop primer (LPB, LPF) using the LAMP designing software, PRIMEREXPLORER V3 (product of Fujitsu Limited), based on a genus-specific nucleic acid sequence of the 18S rRNA genes common to the four species of human malaria parasites, and each species-specific nucleic acid sequence of the 18S rRNA genes of *P. falciparum*, *P. vivax*, *P. malariae* and *P. ovale*. However, in general, the nucleic acid sequences of malaria parasite genes differ greatly from those of other organisms, being rich in AT content. Therefore, existing primer design software was unable to find optimal primer sets, demanding a repetitive trial-and-error process, and causing difficulties in designing each type of primer. Finally, among many combinations of such synthesized primer sets, usable primer sets both high in sensitivity and specificity were found. Thus, the inventors have successfully designed a genus-specific primer capable of detecting the four species of human-infectious malaria parasites at the same time, and specific primers for each of the four species of malaria parasites (*P. falciparum, P. vivax, P. malariae* and *P. ovale*) from each 18S rRNA gene.

Once the nucleic acid sequence of a primer oligonucleotide is determined, the oligonucleotide can be synthesized by known means, for example, by an automatic DNA synthesizer produced by PerkinElmer, Inc.

According to the present invention, examples of a *plasmodium* genus-specific primer set specific to a nucleic acid sequence of the 18S rRNA genes common among the four species of human malaria parasites, and specific primer sets for each of the malaria parasite 18S rRNA gene of *P. falciparum, P. vivax, P. malariae* and *P. ovale* include, for example, seven primer sets as follow primer sets for the genus *plasmodium* and the four species of malaria parasites:

A primer set for the genus *Plasmodium* [F3(SEQ ID NO: 1), B3c(SEQ ID NO: 2), FIP(F1c-F2)(SEQ ID NO: 3), BIP (B1-B2c)(SEQ ID NO: 4), LPF(SEQ ID NO: 5), LPB(SEQ ID NO: 6)];

A primer set for *P. falciparum* [F3(SEQ ID NO: 7), B3c(SEQ ID NO: 8), FIP(F1c-F2)(SEQ ID NO: 9), BIP(B1-B2c) (SEQ ID NO: 10), LPF(SEQ ID NO: 11), LPB(SEQ ID NO: 12)];

A primer set for *P. vivax* [F3(SEQ ID NO: 13), B3c(SEQ ID NO: 14), FIP(F1c-F2)(SEQ ID NO: 15), BIP(B1-B2c) (SEQ ID NO: 16), LPF(SEQ ID NO: 17), LPB(SEQ ID NO: 18)]; [PvFIP-9 (F1c+F2)(SEQ ID NO: 31), PvBIP-9 (B1+B2c) (SEQ ID NO: 32), PvF3-9 (SEQ ID NO: 33), PvB3c-9 (SEQ ID NO: 34), PvLPF-9 (SEQ ID NO: 35), PvLPB-9 (SEQ ID NO: 36)]; or [PvFIP-7(F1c+F2) (SEQ ID NO: 37), PvBIP-7(B1+B2c) (SEQ ID NO: 38), PvF3-7(SEQ ID NO: 39), PvB3c-7 (SEQ ID NO: 40), PvLPF-7 (SEQ ID NO: 41), PvLPB-7(SEQ ID NO: 42)];

A primer set for *P. malariae* [F3(SEQ ID NO: 19), B3c(SEQ ID NO: 20), FIP(F1c-F2)(SEQ ID NO: 21), BIP(B1-B2c) (SEQ ID NO: 22), LPF(SEQ ID NO: 23), LPB(SEQ ID NO: 24)]; and A primer set for *P. ovale* [F3(SEQ ID NO: 25), B3c(SEQ ID NO: 26), FIP(F1c-F2)(SEQ ID NO: 27), BIP(B1-B2c) (SEQ ID NO: 28), LPF(SEQ ID NO: 29), LPB(SEQ ID NO: 30)].

Here, primers each specific to the genus *Plasmodium, P. falciparum, P. vivax, P. malariae* and *P. ovale* are primers capable of specifically amplifying a particular region of the 18S rRNA genes common to said *Plasmodium* species and each particular region of each 18S rRNA gene of *P. falciparum, P. vivax, P. malariae* and *P. ovale*.

Examples of sequences characterized by the genus *Plasmodium* and the four species of malaria parasites subjected to detection/identification using LAMP of the present invention include the 18S rRNA gene sequences of *P. falciparum* (*P. falciparum*: GenBank Accession No. M19173.1, M19173.2, M19172), *P. vivax* (*P. vivax*: GenBank Accession No. U03079, U03080, X13926), *P. malariae* (*P. malariae*: GenBank Accession No. M54897), and *P. ovale* (*P. ovale*: GenBank Accession No. L48986, L48987) deposited at GenBank.

The detection or identification of the genus *Plasmodium* or one of the four species of malaria parasites present in the specimen are conducted by isothermal gene amplification generally in the range of at 60 to 65° C. for 15 minutes to 1 hour, using at least one set of the aforementioned five primer sets, following the procedure of LAMP. That is, DNA collected from specimens such as blood samples and the like is isolated by a known method, and this DNA is amplified using said primer set. The presence of the amplified DNA product can be easily detected by LAMP, or by a general method of electrophoresis.

The aforementioned easy detection includes: 1) visual inspection of the amplification reaction mixture for white turbidity (WO 2001/83817); 2) a method for measuring the fluorescence polarization values of the reaction mixture using a fluorescent substance such as fluorescein, fluorescein isothiocyanate (FITC), X-rhodamine (ROX) or the like (Japanese Unexamined Patent Publication No. 2002-272475), which uses a continuous fluorometer such as an ABI Prism 7700 (product of Applied Biosystems) and the like, allowing for the confirmation of amplification or kinetic analysis; and 3) visual inspection using SYBR Green 2, which uses a fluorescent green dye as an intercalator (WO 2002/103053). By any of these methods, the presence or absence of any amplification products (presence or absence of the target 18S rRNA gene) can be inspected using the naked eye.

According to the present invention, a malaria parasite detection kit capable of detecting any of the genus *Plasmodium, P. falciparum, P. vivax, P. malariae* or *P. ovale* simultaneously or separately can be provided.

The above malaria parasite detection kit can be prepackaged with various types of reagents necessary for detecting nucleic acid amplified using the primer set of the present invention. Specifically, various types of oligonucleotides necessary for the primers or loop primers of the present invention, four species of dNTPs as substrates for nucleic acid synthesis, a template-dependent nucleic acid synthase with strand displacement activity, a buffer or a salt to provide preferable conditions for enzymatic reaction, a protective agent for stabilizing enzymes or templates, and, when indicated, reagent(s) necessary for detecting a reaction product are provided as a kit.

Example of Kit Components:

(1) A reaction mixture containing a primer set for the genus *Plasmodium* [F3 (SEQ ID NO: 1), B3c (SEQ ID NO: 2), FIP (F1c-F2)(SEQ ID NO: 3), BIP(B1-B2c) (SEQ ID NO: 4), LPF (SEQ ID NO: 5), LPB (SEQ ID NO: 6)];

(2) A reagent for the visual detection of fluorescence;

(3) An enzyme mixture solution (including Bst DNA polymerase);

(4) A positive control (for the genus *Plasmodium*); and (5) Distilled water are provided.

The present invention further provides an anti-malaria measure support system and a malaria infection-prevention/treatment measure system.

Malaria-infected patient information includes the number positive for the genus *Plasmodium* that causes malaria in a malaria endemic area, and the carrier rate in the area; and specifically, the information includes, as basic information, subject information such as the name, sex, age, weight, pregnancy or non-pregnancy status, family structure, residential address, birthplace, names of pre-existing diseases, names of drugs being taken, history of drug side effects, etc., of individual subjects residing in the endemic area, together with their positivity or negativity for the genus *Plasmodium* and the acquisition or non-acquisition of resistance to malaria therapeutic agents, and the malaria parasite carrier rate in the area. The means for inputting and storing malaria-infected patient information are, for example, computer input devices and storage devices.

The carrier rate for the genus *Plasmodium* that causes malaria in a malaria endemic area is expressed as a percentage obtained by dividing the number of subjects positive for the genus *Plasmodium* by the number of subjects of the genus

*Plasmodium* detection test and multiplying the resultant quotient by 100. In the anti-malaria measure support system of the present invention, for example, a genus *Plasmodium* detection method using LAMP can be particularly preferably used in malaria endemic areas. In a subject who has resided in a malaria endemic area for a long period and has acquired immunity (resistance) against malaria, the number of parasites in the subject's blood is as small as about one hundredth to about one thousandth of that in a patient with malarial fever. Microscopic detection of such a small number of parasites with high sensitivity is very difficult. Also, after malaria infection and the latent period, in the early stages of the period in which a fever develops due to the appearance of malaria parasites in the blood, the number of parasites is small and therefore microscopic detection of the parasites is extremely difficult. Microscopic detection with high sensitivity is also very difficult when a malaria therapeutic agent has already been administered and the number of parasites in the subject's blood has been remarkably reduced by the effects of the therapeutic agent.

In many malaria endemic areas, satisfactory DNA extractors do not exist or are not provided. In the preparation of DNA for PCR, when highly pure DNA cannot be obtained using an extraction kit, PCR cannot be performed because PCR does not occur due to the inhibitor of the DNA amplification enzymes for PCR, which is present in blood.

In the genus *Plasmodium* detection method used in the anti-malaria measure support system of the present invention, the DNA sample can be very easily obtained by, for example, collecting a very small amount of blood from the subject's finger tip, boiling the blood in boiling water for 10 minutes, and centrifuging the blood at 10000 rpm for 1 minute to obtain the supernatant, which can be used as DNA. Therefore, the method in which the genus *Plasmodium* in a specimen are detected using the genus *Plasmodium* detection primer set of the present invention, which can amplify a specific region of the 18S rRNA gene sequence of *Plasmodium*, can be advantageously used in malaria endemic areas. Further, when research is conducted not only on subjects in a malaria endemic area, but also on the rate of mosquitoes collected in an endemic area that carry malaria parasites to obtain important data for malaria epidemic prediction based on research on mosquitoes carrying malaria parasites, since DNA for use in the method of the present invention can be more easily extracted from mosquitoes than DNA for PCR, the frequency of the detection of the genus *Plasmodium* in specimens, obtained using a genus *Plasmodium* detection primer set of the present invention, which can amplify a specific region of the 18S rRNA gene sequence of *Plasmodium*, can be stored in a storage device as a piece of information for malaria epidemic prediction in the malaria infection-prevention public health measure database.

The method for detecting or identifying the genus *Plasmodium* or four species of malaria parasites according to the present invention is simpler, less expensive, more easily operable, and has higher sensitivity and higher specificity, than microscopy and PCR, and therefore can be used most preferably in endemic areas.

Public health measures for malaria infection endemic areas based on malaria-infected patient information include the following (1) to (4): (1) eliminating, from the area, environments where mosquitoes are likely to breed, and eliminating sources of mosquitoes by exterminating mosquitoes and mosquito larvae bred in stagnant water; (2) spraying an insecticide in houses, sheds, etc., providing doors and windows with wire screens, and preferably, installing air-conditioners in houses if the residents of the houses can afford them; (3) providing beds with mosquito nets (mosquito nets with long-lasting effects: LLIN, Sumitomo Chemical Co., Ltd.) impregnated with an insecticide (pyrethroid-based insecticide: permethrin), applying to human skin an insect repellent spray containing an insect repellent (diethyltoluamide: DEET), and taking measures such as wearing long-sleeved shirts after sunset, spraying clothes with an insecticide, etc.; and (4) prophylactically administering a therapeutic agent, such as a mixture of mefloquine and artesunate, chloroquine, artemisinin, quinine, doxycycline, or the like, based on information about malaria parasites occurring with high frequency in the endemic area and drug-resistant strains, so that the malaria therapeutic agent also serves as a malaria prophylactic agent.

For infection-positive patients, malaria parasite extermination (treatment) with a malaria therapeutic agent is taken into consideration. Information about malaria parasites occurring with high frequency in the endemic area and drug-resistant strains is available from the websites of the departments of health of countries with endemic areas; the Japan Health Sciences Foundation, policy innovative drug development general research project, research group on chemotherapy of tropical diseases, the Guidance for Parasitic Disease Chemotherapy, revised version 6.0 (2007); and the guidelines of the Expert Meeting on Malaria Chemoprophylaxis published on March, 2005. The malaria therapeutic agent can be easily selected according to the species of malaria parasites detected or identified by the method of the present invention, based on known standards for selecting therapeutic agents.

The priority of measures, which indicates which of the above public health measures (1) to (4) should be given priority in selection, is determined considering the degree of malaria prevalence in the area, economic conditions of the country, environmental and economic conditions of the residents, etc. The measure (1), which can be taken by the country, local government, autonomous body, or the like, should be given priority, and then the measures (2) and (3), which can be easily taken by individual subjects and other residents, are desirable.

The measure (4), prophylactic administration of a therapeutic agent, has a lower priority considering the general economic conditions of residents in malaria endemic areas, and is likely to be limited to residents with special needs, such as infants, pregnant women, etc. The measure (4) is not sufficient at present. The priority of measures varies depending on the endemic area, and may be, for example, preferably (1)>(2)=(3)>(4), and from a practical point of view, (2)=(3)>(4)>(1). Such measure priority is extracted in a public health measure extraction section (e.g., a program) in view of the degree of malaria prevalence, economic conditions of the country, environmental and economic conditions of the residents, etc., and is displayed on a public health measure display section (e.g., display).

The information stored in the malaria infection-prevention public health measure guide database, into which the public health measure selection information for the inputted malaria parasite-infected area has been inputted, may include, as described above, the type and frequency of malaria that is actually endemic in the area, information about drug-resistant strains, information about the public health measures (1) to (4), instruction information about the measures, malaria epidemic prediction, malaria diagnosis methods, and information about drugs selected for respective species of infecting malaria parasites.

Using DNA extracted from a subject, the malaria parasite detection method of the present invention is carried out to obtain infected patient information about the presence or absence of malaria infection in subjects; and this information is checked against the public health measures for the malaria infection endemic area, and their priority, obtained from the public health measure extraction section that extracts the priority of the public health measures from the malaria infection-prevention public health measure guide database, and the public health measure display section that displays the public health measures extracted in the public health measure extraction section together with their priority. Thus, the public health measures that should be taken by local governments or individual subjects in the endemic area can be carried out sequentially or simultaneously. Further, the effects of such public health measures can be stored as information in the malaria infection-prevention public health measure guide database. This can update the malaria infection-prevention public health measure guide database. The anti-malaria measure support system of the present invention can thus be provided to a malaria endemic area.

The subject information including information about the presence or absence of infection with malaria parasites in subjects can be managed and obtained by a conventional technique using a PC (personal computer) or a cellular phone, a facsimile, etc. The information to be stored in the malaria infection-prevention public health measure guide database can be obtained from Internet websites using a PC or a cellular phone, or from brochures.

In the anti-malaria measure support system of the present invention, the means for inputting and storing malaria therapeutic agent information for specifying a malaria therapeutic agent that acts on infection with one or a plurality of four species of malaria parasites indicates means for storing information including the effects of drugs, drug names, generic names, areas in which respective drugs are preferably applied, administration periods, dosages, types and frequencies of side effects, severity of side effects, contraindications, information about infants and pregnant women, information about concomitant use with other drugs, drug prices, etc., into the "treatment guide database", considering the actual appearance of drug-resistant strains in each malaria endemic area, and the degree thereof, or considering the clinical symptoms of each type of malaria, age, and pregnancy or non-pregnancy status of the patient.

It is important that patients with a fever caused by malaria infection be differentially diagnosed from patients with other infections such as influenza, since malaria infection, and in particular *P. falciparum* infection, results in a serious outcome if treatment is delayed. Therefore, prompt, highly sensitive, and highly specific differential diagnosis is desired. In particular, as described above, satisfactory DNA extractors do not exist or are not provided in many malaria endemic areas, and in the early stages of a fever, the number of malaria parasites is so small that microscopic identification of malaria parasites is not easy.

The method for identifying *P. falciparum, P. vivax, P. malariae,* or *P. ovale* using a primer set comprising a sequence specific to *P. falciparum, P. vivax, P. malariae,* or *P. ovale* according to the present invention, or the identification/detection kit therefor, makes it possible to identify infection with one or a plurality of four species of malaria parasites more easily, more rapidly, and with higher sensitivity and higher specificity, than other identification methods such as PCR and microscopy.

Further, the malaria parasite detection/identification method of the present invention enables monitoring of the therapeutic effects of the administration of malaria therapeutic agents to malaria-infected patients.

The system of the present invention is based on the malaria parasite-specific detection or identification technique. The "patient information input means for inputting and storing patient information including information about the pathogen of malaria infection in a patient with a fever in a malaria endemic area" is means for inputting and memorizing/storing subject information including information about the pathogen of malaria infection in a patient with a fever in a malaria endemic area, and the name, age, sex, weight, pregnancy or non-pregnancy status, family structure, residential address, birthplace, names of pre-existing diseases, names of the drugs being taken, drug side-effect history, etc. of the patient with a fever, into a PC (personal computer). The input and memorizing/storage can be performed from a PC or a cellular phone, or as facsimile information from medical facilities and hospitals, based on information obtained from endemic areas.

The "patient information input means for inputting and storing patient information including information about the pathogen of malaria infection in a patient with a fever in a malaria non-endemic area" is the same as the "patient information input means for inputting and storing patient information including information about the pathogen of malaria infection in a patient with a fever in a malaria endemic area" except that the patient with a fever is "a patient with a fever in a malaria non-endemic area".

In the above, "comprising a treatment guide database into which, according to indices of efficacy against malaria parasites detected in a subject, malaria therapeutic agent selection information to be inputted together with a priority that indicates which malaria therapeutic agent should be given priority in selection for use against the malaria parasites; a malaria therapeutic agent extraction section that extracts, according to the information about the pathogen of malaria infection in the subject, malaria therapeutic agents to be administered and the priority thereof, from the treatment guide database; and a malaria therapeutic agent display section that displays the malaria therapeutic agents extracted in the above malaria therapeutic agent extraction section, together with the priority thereof" indicates a process in which a clinical practitioner or a hospital doctor who has obtained information about the pathogens of malaria infection in a patient with a fever in a malaria endemic or non-endemic area displays which malaria therapeutic agent should be given priority in selection for use against the infecting malaria parasites, considering the species of malaria parasites infecting the patient with a fever, the symptoms of the patient, and other conditions, using an index of the efficacy of each therapeutic agent, such as the specificity of effects on infections with *P. falciparam, P. vivax, P. malariae, P. ovale*, or on complex infections with two or more species of these malaria parasites, and further checking the pathogen information including the source of malaria infection and other conditions of the patient with a fever, against the malaria therapeutic agent information stored in the "treatment guide database" including, for example, the effects of drugs, drug names, generic names, areas in which respective drugs are preferably applied, specificity of action, administration periods, dosages, types and frequencies of side effects, severity of side effects, contraindications, information about infants and pregnant women, information about concomitant use with other drugs, drug prices, etc.

According to the anti-malaria measure support system of the present invention, clinical practitioners and hospital doctors can check information about the pathogen of malaria infection in a patient with a fever against the malaria therapeutic agent guide database in a PC or via a cellular phone to have a conventional software to operate, thereby obtaining a display of which malaria therapeutic agent should be given priority in selection, or which malaria therapeutic agents should be used in combination.

The above-mentioned malaria therapeutic agent information can be stored in the "treatment guide database", referring to the Japan Health Sciences Foundation, policy innovative drug development general research project, research group on chemotherapy of tropical diseases; the Guidance for Parasitic Disease Chemotherapy, Revised Version 6.0 (2007); the guideline of Expert Meeting on Malaria Chemoprophylaxis published on March, 2005; and the malaria treatment guideline of the CDC (Centers for Disease Control and Prevention) in the U.S.

For example, since increasing numbers of $P.$ $falciparum$ strains have become chloroquine-resistant, concomitant administration of mefloquine and artesunate is considered the malaria treatment to be given priority in selection in Thailand and developed countries. On the other hand, in areas where drug prices are reflected, second-generation drugs of fansidar take priority in selection in some cases. Against $P.$ $vivax$ and $P.$ $ovale$, chloroquine takes priority in selection in the erythrocytic stage that causes clinical symptoms such as a fever, and then a two-week course of primaquine administration is selected for complete cure and recurrence prevention. Further, priority is given to the selection of chloroquine for use against $P.$ $malariae$.

Such information is also stored in the "malaria infection-prevention public health measure guide database".

The information about the results of the malaria treatment of a patient with a fever with the drug selected as a malaria therapeutic agent to be given priority in selection, using the anti-malaria measure support system of the present invention, is fed back to the "malaria parasite treatment guide database" and the "malaria infection-prevention public health measure guide database", and stored as updated information.

Thus, an anti-malaria measure support system can be provided in which information about the pathogen of malaria infection in a patient with a fever can be obtained easily, rapidly, and with high sensitivity and high specificity, by subjecting a specimen extracted from a patient with a fever in a malaria endemic area, or a patient with a fever in a non-endemic area, to the method for identifying infection with a single or a plurality (complex) of four species of malaria parasites according to the present invention; and in which a clinical practitioner or a hospital doctor in a malaria endemic area or non-endemic area can check such information against the malaria parasite treatment guide database to select a preferable therapeutic agent and administration method that should be given priority in selection, for a patient who has developed a fever due to malaria infection, and can apply such a drug and method to the treatment of the malaria-infected patient with a fever.

From the overall viewpoint of malaria infection-prevention public health measures in a malaria endemic area and the treatment of a malaria-infected patient with a fever in a malaria endemic area or non-endemic area, the present invention can also provide an anti-malaria measure support system for malaria eradication in the endemic area, by combining: the obtainment of malaria-infected patient information in a malaria endemic area using the method for detecting malaria parasites according to the present invention; the obtainment of information about the pathogen of malaria infection in a patient with a fever in a malaria endemic area or non-endemic area using the anti-malaria measure support system for local governments, autonomous bodies, or residents in a malaria endemic area, in which a malaria infection-prevention public health measure database is used, and the method or kit for identifying infection with a single or plurality of four species of malaria parasites according to the present invention; and an anti-malaria measure support system in which a clinical practitioner or a hospital doctor in a malaria endemic area or non-endemic area using the malaria parasite treatment guide database can select a preferable therapeutic agent and administration method that should given priority in selection for a malaria-infected patient with a fever and apply the drug and method to the treatment of the malaria-infected patient with a fever.

The above pieces of information can be inputted and stored using a PC, and can be displayed through a PC or a cellular phone, or through a paper brochure, in the area.

The present invention can further provide a malaria infection-prevention measure system for travelers from a malaria non-endemic area to a malaria endemic area. The present invention can provide a malaria infection-prevention measure system for persons who plan to travel to a malaria endemic area, the system comprising means for obtaining, from the anti-malaria measure support system described above, the state of the implementation of public health measures in the malaria endemic area, information about the pathogens of malaria infection in the endemic area, and the state of the treatment of infected patients; means for selecting a malaria prophylactic/therapeutic agent from a malaria parasite treatment guide database; and means for administering the selected agent before travel.

The above pieces of information are easily available from Internet websites using a PC or a cellular phone, or as information provided in brochures from the malaria endemic area or national governmental organizations. Using the malaria infection-prevention measure system for persons who plan to travel to a malaria endemic area, it is possible for persons who plan to travel to a malaria endemic area to know beforehand the malaria infections that are endemic in the area and the state of the appearance of drug-resistant strains. Thus, to prevent malaria infection, the persons can take, before travel, a preferable malaria therapeutic agent to be given priority in selection for use against the malaria infections that are endemic in the area, so that even if the persons should be infected with malaria, symptoms due to malaria infection, such as fever, can be reduced at an early stage and serious conditions can be prevented, making it possible to exterminate malaria parasites in the blood of such persons at an early stage.

The present invention can further provide a malaria infection-prevention/treatment measure system for returnees from a malaria endemic area, the system comprising: means for obtaining, from the anti-malaria measure support system, the state of the implementation of public health measures in the malaria endemic area, information about the pathogens of malaria infection in the endemic area, and the state of the treatment of infected patients; means for selecting a malaria prophylactic/therapeutic agent from a malaria parasite treatment guide database; and means for administering the selected agent after returning from the malaria endemic area. According to the present invention, since the latent period before the appearance of clinical symptoms, such as a fever, varies from 1 week to 40 days depending on the species of the infecting malaria parasites, when a returnee has been infected with malaria parasites immediately before returning from a malaria endemic area and in the case where the returnee is aware of having been bitten by a mosquito immediately before returning, a preferable malaria therapeutic agent against malaria parasites that may cause infection can be selected and administered referring to information from the anti-malaria measure support system, so that symptoms due to malaria infection, such as a fever, can be reduced at an early stage and serious conditions can be prevented even if the returnee has been infected with malaria, thereby making it possible to exterminate malaria parasites in the blood of the returnee from a malaria endemic area at an early stage.

The present invention can also provide a malaria infection-prevention/treatment measure system for returnees from a malaria endemic area, in which, in the above-mentioned malaria infection-prevention/treatment measure system for returnees from a malaria endemic area, when a returnee from a malaria endemic area has a fever, the identification of *P. falciparum, P. vivax, P. malariae*, or *P. ovale* is performed to select and administer a malaria therapeutic agent that should be given priority in selection.

Further, the use of the malaria parasite detection/identification method of the present invention in the malaria infection treatment measure system of the present invention makes it possible to monitor the therapeutic effects of malaria therapeutic agent administration to malaria-infected patients.

In the above, when the returnee develops a fever before administration of a malaria therapeutic agent, a specimen from the returnee with a fever is subjected to the method for identifying four species of malaria parasites according to the present invention, to identify *P. falciparum, P. vivax, P. malariae, P. ovale*, or a plurality (complex) thereof, and select and administer a malaria therapeutic agent that should be given priority in selection for use against the malaria parasites. The malaria infection treatment measure system of the present invention can thus provide a suitable malaria infection treatment method, and a method for monitoring the therapeutic effects thereof.

Figure 3:
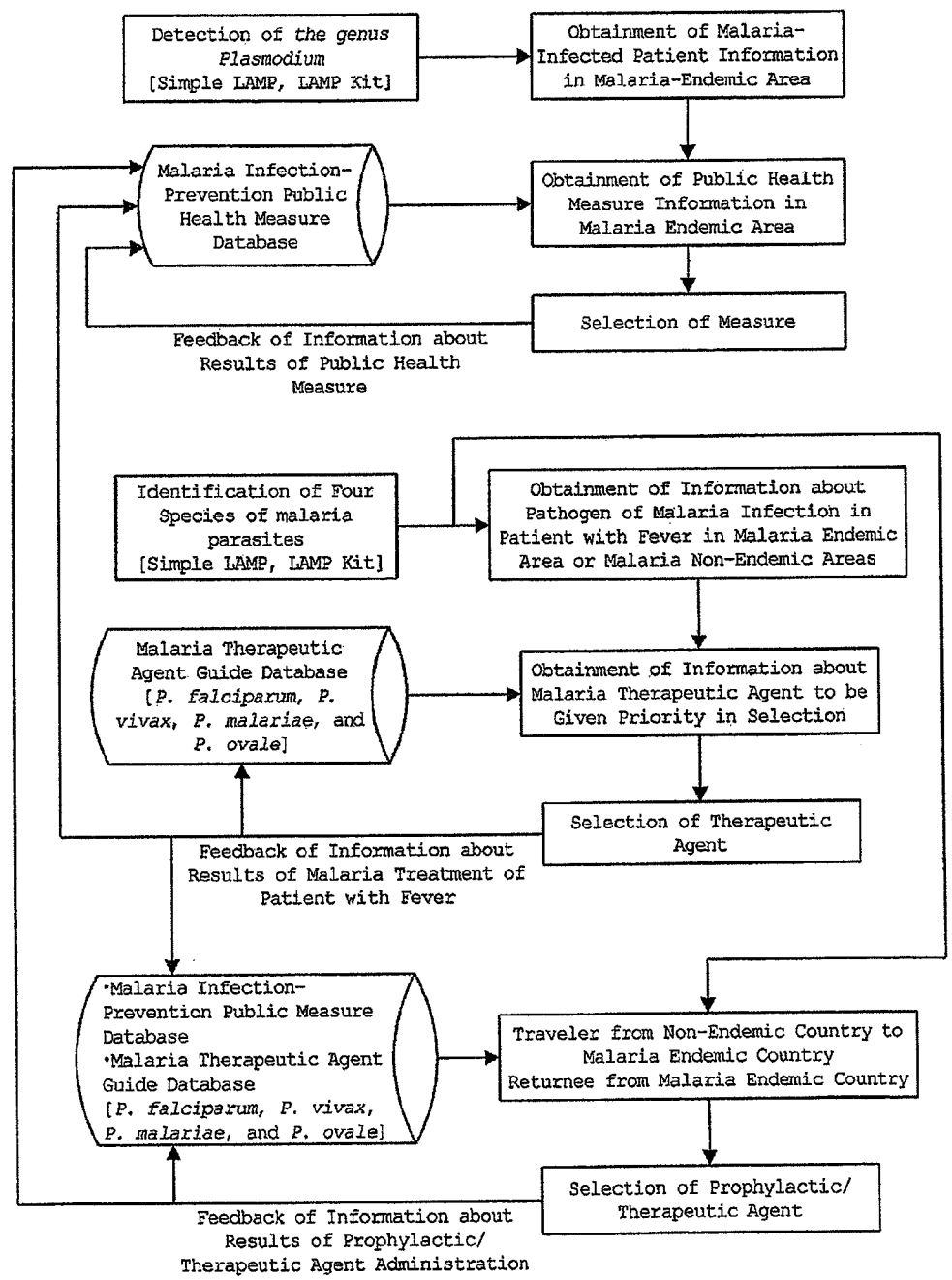
FIG. 3 is a flow chart of the process of the anti-malaria measure support system based on the principle of the present invention.

As shown in FIG. 3, information about the results of public health measures, information about the results of malaria treatment for patients with a fever, and information about the results of prophylactic/therapeutic agent administration are fed back into respective databases.

EXAMPLES

The following Examples illustrate the present invention in further detail, but are not intended to limit the scope of the present invention.

Example 1

Materials and Methods:

Sixty-eight samples that were positive for malaria parasites by microscopy were collected from patients who had visited malaria clinics in Mae Sod and Mae Kasa, northwestern Thailand. In addition, 53 samples that were negative by microscopy were collected from residents in a malaria endemic area of Kanchanaburi, western Thailand.

The blood samples were tested by microscopy and LAMP. Each test was carried out by independent researchers (microscopy in the Armed Forces Research Institute of Medical Sciences, Thailand, and LAMP in Ehime University, Japan), blinded to the origin of the specimens and the laboratory results, and finally the test results were compared and analyzed.

Microscopy:

Thick peripheral blood smears were examined under 1,000× magnification by microscopists with extensive experience in the identification of malaria parasites. The parasite density was counted per 500 leukocytes and was then calculated as the number of parasites per microliter by assuming a leukocyte count of 7,000/µl. The initial thick film was considered negative if no parasites were seen after 500 leukocytes were counted.

DNA Extraction:

The DNA template for LAMP was prepared as described in Plowe, C., et al. (Am. J. Trop. Med. Hyg. (1995) Vol. 52: 565-568). Twenty-five to fifty microliters of the human blood was blotted as single spot and dried on filter paper. A single blood-spot from each filter paper was excised, then incubated for 4 hours at room temperature and/or overnight at 4° C. in 1 ml of 0.5% saponin in phosphate-buffered saline (PBS). The filter paper was washed for 30 minutes in PBS at 4° C. and transferred into new tubes containing 200 µl of 5% CHELEX-100 cation exchange resin (Bio-Rad, Hercules, Calif.), and vortexed for 30 seconds. The mixture was incubated at 56° C. for 15 minutes, vortexed for 30 seconds, and heated at 100° C. for 15 minutes to elute the DNA, vortexed, and centrifuged (10,000×g for 5 minutes). The supernatant was either used immediately after the reaction, or stored in aliquots at −20° C.

LAMP Conditions:

LAMP primer sets for *P. falciparum* described in Poon et al. (Non-Patent Document 1) were used. The remaining *Plasmodium* genus- and species-specific LAMP primer sets were attempted to be designed using the LAMP Primer Designing Software PrimerExplorer V3 (manufactured by Fujitsu Ltd.). However, the nucleotide sequences of the genes of malaria parasites are generally greatly different from those of organisms of other species and have a high AT content; therefore, it was impossible to find optimal primer sets using the above primer designing software. Accordingly, many trials and errors were necessary, encountering difficulties in designing the primers. Finally, however, primer sets having sensitivity and specificity sufficient for practical use were able to be found among the synthesized primer sets with numerous combinations. Thus, a genus-specific primer set that is capable of detecting the four species of the genus *Plasmodium* that infect humans at a time, and primer sets each specific to each of the four species of malaria parasites (*P. falciparum, P. vivax, P. malariae*, and *P. ovale*) were successfully designed based on the genus- and species-specific nucleotide sequences of the 18S rRNA genes.

After the nucleotide sequences of the oligonucleotides were designed as above, primers were synthesized by a known method, for example, using Automated DNA Synthesizer, manufactured by Perkin-Elmer.

The location and nucleotide sequence of each primer are shown in FIG. 1.

More specifically, primer sets for the genus *Plasmodium* and primer sets for the respective four *Plasmodium* species were used:

primer sets for the genus *Plasmodium* [(F3 (SEQ ID NO: 1), B3c (SEQ ID NO: 2), FIP(F1c-F2)(SEQ ID NO: 3), BIP (B1-B2c)(SEQ ID NO: 4), LPF(SEQ ID NO: 5), LPB(SEQ ID NO: 6)];

primer sets for *P. falciparum* [F3 (SEQ ID NO: 7), B3c (SEQ ID NO: 8), FIP(F1c-F2)(SEQ ID NO: 9), BIP(B1-B2c) (SEQ ID NO: 10), LPF(SEQ ID NO: 11), LPB(SEQ ID NO: 12)];

primer sets for *P. vivax* [F3 (SEQ ID NO: 13), B3c (SEQ ID NO: 14), FIP(F1c-F2)(SEQ ID NO: 15), BIP(B1-B2c)(SEQ ID NO: 16), LPF(SEQ ID NO: 17), and LPB(SEQ ID NO: 18)];

primer sets for *P. malariae* [F3 (SEQ ID NO: 19), B3c (SEQ ID NO: 20), FIP(F1c-F2)(SEQ ID NO: 21), BIP(B1-B2c)(SEQ ID NO: 22), LPF (SEQ ID NO: 23), LPB (SEQ ID NO: 24)];

primer sets for *P. ovale* [F3 (SEQ ID NO: 25), B3c (SEQ ID NO: 26), FIP(F1c-F2)(SEQ ID NO: 27), BIP(B1-B2c)(SEQ ID NO: 28), LPF (SEQ ID NO: 29), LPB (SEQ ID NO: 30)].

The LAMP reaction was performed with a Loopamp DNA amplification kit (Eiken Chemical Co., Ltd., Tokyo, Japan).

Reaction mixtures (25 µl) contained 1.6 to 2.4 µM of each FIP and BIP, 0.2 µM of each F3 and B3c, 0.8 µM of each LPF and LPB, 2× reaction mix (12.5 µl), Bst DNA polymerase (1 µl), and 1 to 2 µl of DNA sample (corresponding to approximately 0.125 to 0.5 µl of blood).

The LAMP reaction was performed at 60° C. for 100 minutes, then the enzyme was inactivated at 80° C. for 2 minutes.

Analysis of LAMP Products:

The LAMP reaction causes turbidity in the reaction tube, proportional to the amount of amplified DNA. Therefore, the turbidity was observed with the naked eye. To confirm the sensitivity of LAMP, turbidity was also monitored by a Loopamp real-time turbidimeter (RT-160C, Eiken Chemical Co., Tokyo, Japan).

For further confirmation, 5 µl of LAMP product was electrophoresed at 100 V in a 3% agarose gel, followed by staining with ethidium bromide, using MassRuler™ DNA ladder marker (Fermentas Inc., Hanover, Md.). The specificity of LAMP was evaluated by restriction enzyme digestion of the amplified product.

Based on the restriction enzyme maps of the target sequences of each LAMP product, restriction enzyme, DdeI was selected for restriction enzyme analysis of the *Plasmodium* genus-specific LAMP products, HpyCH4V for *P. falciparum, P. vivax,* and *P. malariae,* and restriction enzyme, AluI for *P. ovale.* Following overnight digestion at 37° C., the digested products were analyzed by agarose gel electrophoresis.

Diagnostic Threshold of LAMP Results:

The formation of LAMP reaction products was monitored using a Loopamp real-time turbidimeter. Most of the positive samples tested multiple times showed positivity within 1 hour. Therefore, a sample having turbidity greater than or equal to the threshold value by turbidimeter within 1 hour was considered positive.

Positive Control Plasmid DNA and Sequencing:

For sensitivity assessment, plasmids containing the target region of the 18S rRNA gene for LAMP reaction were constructed for each species. Target DNA sequence was amplified with two LAMP primers (F3 and B3c) by PCR, then cloned into the pCR® 2.1-TOPO TA Cloning vector (Invitrogen, Carlsbad, Calif.).

The nucleotide sequences were determined using an automated DNA sequencer (ABI PRISM® 310 Genetic Analyzer, Applied Biosystems).

Analytical Sensitivity and Specificity of LAMP:

To establish the minimum copy number (lower detection limit) of target gene sequence detectable by LAMP, positive control plasmid DNAs were used as templates. The standard curve for LAMP was constructed using 10-fold serial dilutions of plasmid DNA ($10^6$ to 1 copy) into sterile water. For each standard, the copy number was plotted against the threshold time. The resulting plots were analyzed by linear regression, and the statistical significance of $\gamma^2$ values was analyzed by ANOVA (Free Statistics and Forecasting Software v1.1.21). Probabilities less than 0.05 were considered statistically significant. The specificity of the genus- and species-specific LAMP was evaluated on each control plasmid DNA and *P. falciparum* genomic DNA (gDNA) purified from NF54 strain, *P. vivax* gDNA from Sal-I strain, *P. malariae* gDNA from Uganda strain, and *P. ovale* CDC type gDNA from CDC strain.

Results of Analytical Sensitivity and Specificity of *Plasmodium* genus- and Species-Specific LAMP:

The sensitivity of LAMP for the genus *Plasmodium* and four species of malaria parasite, *P. falciparum, P. vivax, P. malariae,* and *P. ovale,* was 10 copies for *P. malariae* and *P. ovale,* and 100 copies for the genus *Plasmodium, P. falciparum,* and *P. vivax.*

The specificity of each LAMP reaction was further confirmed by restriction enzyme digestion of LAMP products. The sizes of the resultant digestion products were in good agreement with the predicted sizes.

Clinical Sensitivity and Specificity:

The clinical sensitivity and specificity of the *Plasmodium* LAMP were calculated on 121 whole-blood samples with microscopy as the reference standard method. Sensitivity was calculated as (number of true positives)/(number of true positives+number of false negatives), and specificity was calculated as (number of true negatives)/(number of true negatives+number of false positives).

Clinical Sensitivity and Specificity: Comparison of Microscopy and LAMP:

The results of microscopy and LAMP are given in Table 2.

Among 68 patients who were positive for malaria parasite by microscopy, 12 patients were diagnosed with *P. falciparum* infection, 34 with *P. vivax* infection, 12 with *P. malariae* infection, 5 with *P. ovale* infection, and 5 with mixed *P. falciparum* and *P. vivax* infection. The remaining 53 samples were negative by microscopy.

LAMP using the genus-specific primer set detected malaria parasites in 67 samples out of 68 samples positive by microscopy (98.5% sensitivity). Among the 53 samples that were negative by microscopy, genus-specific LAMP detected malaria parasites in 3 samples (94.3% specificity).

The 3 samples positive by LAMP but negative by microscopy were re-tested by LAMP.

All three samples were again positive by genus-specific LAMP; one was diagnosed with *P. falciparum* and the other two with *P. vivax* by species-specific LAMP.

It is thus presumed that LAMP is more sensitive than microscopy and can reduce the false negative diagnosis, which may clinically cause oversights, to the least possible degree.

All 12 samples that were positive for *P. falciparum* by microscopy were also positive for *P. falciparum* by species-specific LAMP. Among 34 samples positive for *P. vivax* by microscopy, 2 samples were diagnosed with *P. ovale* infection, and 1 with mixed *P. falciparum* and *P. vivax* infection, by LAMP. Among 12 samples positive for *P. malariae,* 1 sample was diagnosed with *P. ovale,* and 1 sample with mixed *P. malariae* and *P. vivax.*

The above results indicate that the new LAMP malaria diagnosis method developed by the present inventors has higher sensitivity and higher specificity than microscopy, and is an advantageous method for detecting the four species of human malaria parasites.

The average detection time by LAMP was as follows.

Genus-specific LAMP: 25.7±4.9 minutes (mean±SD; 19.4 to 52.9 minutes);

*P. falciparum*-specific LAMP: 31.7±4.8 minutes (25.8 to 44.9 minutes);

*P. malariae*-specific LAMP: 30.6±5.2 minutes (25.4 to 46.9 minutes);

*P. vivax*-specific LAMP: 34.8±4.8 minutes (30.5 to 46.6 minutes); and

*P. ovale*-specific LAMP: 36.1 ±6.8 minutes (29.9 to 49.8 minutes).

These results show that LAMP can make diagnosis in a period of time that is remarkably shorter than the amplification time of nested PCR.

Example 2

The primer sets for detecting the genus *Plasmodium* and *Plasmodium* species according to the present invention, and the method for detecting or identifying the genus *Plasmodium*, *P. falciparum*, *P. vivax*, *P. malariae*, and *P. ovale* separately or simultaneously using the primer sets, were subjected to comparative tests with PCR and microscopy in a malaria clinic in Mae Sod, northwestern Thailand, where malaria is endemic.

A comparison was also made between the above method carried out using equipment specially designed for LAMP, and the above method carried out by a procedure that can be rapidly and easily performed in a malaria endemic area.

Eighteen samples that were positive for malaria parasites by microscopy (the percent parasitemia: 0.04% to 0.31%) were used; and one sample that appeared to be a technical error was excluded from the Example beforehand.

Boiling method was used to extract DNA from patient samples for the rapid and easy detection and identification of malaria parasites in a malaria endemic area, according to the present invention (the genus *Plasmodium*, *P. falciparum*, *P. vivax*, *P. malariae*, and *P. ovale* can be detected simultaneously). Specifically, 50 µl of distilled water (D.W.) was added to 50 of a blood sample, and the resulting mixture was boiled at 99° C. for 5 minutes, followed by centrifugation (5415D, produced by Eppendorf; 16,000×g) to obtain a supernatant.

Subsequently, 2 µl of the above-obtained supernatant containing DNA was added to 23 µl of a reaction mixture containing 1 µl of Bst DNA polymerase (Epicentre Biotechnologies), 12.5 µl of 2 x reaction mix, 1.6 to 2.4 µM of FIP and BIP in the primer sets obtained in Example 1, 0.2 µM of F3 and B3c in the primer sets obtained in Example 1, and 0.8 µM of LPF and LPB in the primer sets obtained in Example 1, and reacted at 60° C. for about 60 minutes in a constant-temperature water bath (Thermominder SM-05R, produced by TAITEC) capable of containing 96×2 (total 192) tubes.

The presence or absence of turbidity in the reaction product was visually observed directly to detect the presence or absence of infection with the genus *Plasmodium* and identify which of the *P. falciparum*, *P. vivax*, *P. malariae*, or *P. ovale* causes the infection.

Separately, the reaction mixture containing DNA extracted from each of the above samples was reacted at 60° C. for about 60 minutes using a Loopamp real-time turbidimeter (LA-320C, produced by Eiken Chemical Co., Ltd.) to monitor the formation of the reaction product in real time.

Further, for comparison with PCR with respect to the diagnosis of malaria species, nested PCR was performed on the same samples. Since strict conditions are required for a PCR reaction, the PCR reaction may be inhibited when DNA extracted from a clinical sample by boiling method is used as it is. Thus, dried blood on filter paper obtained in the malaria clinic was brought to a well-equipped laboratory in Bangkok, and DNA was extracted using a DNA extraction kit (QIAamp DNA Mini Kit, produced by QIAGEN) and subjected to PCR. In the nested PCR, two rounds of PCR were each performed for 2 hours, for a total of 4 hours. Thereafter, the obtained sample was subjected to agarose gel electrophoresis and stained with fluorescence, and detection was performed for a total of 5 hours.

As a result, of the 18 samples that were positive for malaria parasites by microscopy, in the detection of the presence or absence of infection with the genus *Plasmodium* using the primers for the genus *Plasmodium*, 18 were positive when the samples were tested using the Loopamp real-time turbidimeter specially designed for LAMP, and 18 were also positive when the samples were tested by reacting in a constant-temperature water bath followed by visual observation. The results of the two tests agreed 100%.

Table 1 compares the test results for microscopy, nested PCR, and LAMP for the diagnosis of malaria species using *Plasmodium* species-specific primers; and the results using an amplifier specially designed for LAMP, with the results of the visual observation after the reaction in a constant-temperature water bath.

TABLE 1

| | | LAMP | |
| --- | --- | --- | --- |
| Sample (Percent parasitemia) | PCR | Specially designed amplifier | Constant-temperature water bath + visual observation |
| Pf (0.12-0.28%) | + | 3 (N.D.2) | 5 | 5 |
| Pv (0.04-0.31%) | + | 12 | 11 | 11 |
| Pv + Po (00.8, 0.04%) | Pv+ Po− | 1 1 | 1 1 | 1 1 |

As is apparent in Table 1, with respect to *P. falciparum*, only 3 samples were subjected to PCR. In the table, Pf indicates *P. falciparum*, Pv indicates *P. vivax*, and Po indicates *P. ovale*.

As a result, in one sample diagnosed by microscopy as being infected with both *P. vivax* and *P. ovale*, both PCR and LAMP (both the test using an amplifier specially designed for LAMP, and the test using visual observation after the reaction in a constant-temperature water bath) detected *P. vivax*, but not *P. ovale*, indicating that the microscopy diagnosis was an error.

That is, in the comparative test, 17 of the 18 LAMP reaction results matched the microscopy results (94% agreement). This means that the LAMP reaction results agreed 100% with the microscopy results, if the above-mentioned one reaction result in disagreement with the microscopy result is excluded. These results reveal that the primer sets for detecting the genus *Plasmodium* and *Plasmodium* species according to the present invention, and the method for detecting or identifying the genus *Plasmodium*, *P. falciparum*, *P. vivax*, *P. malariae*, and *P. ovale* separately or simultaneously using these primers, agreed 100% with the microscopy diagnoses in the detection and identification of *Plasmodium* parasite infection; and the test results using an amplifier specially designed for LAMP agreed 100% with the visual observation results after the reaction in the constant-temperature water bath. In the diagnoses of malaria species, the primer sets and method agreed 100%, and achieved sensitivity equivalent to PCR.

It was demonstrated that, for the primer sets for detecting the genus *Plasmodium* and *Plasmodium* species according to the present invention, and the method for detecting or identifying the genus *Plasmodium*, *P. falciparum*, *P. vivax*, *P. malariae*, and *P. ovale* separately or simultaneously using the primer sets, especially in a malaria endemic area, DNA can be extracted by boiling method, which is rapid, simple, and inexpensive, and a DNA amplification reaction can be carried out using a constant-temperature water bath so that a large number of samples can be treated inexpensively.

The primer sets for detecting the genus *Plasmodium* and *Plasmodium* species according to the present invention and the method for detecting or identifying the genus *Plasmodium*, *P. falciparum*, *P. vivax*, *P. malariae*, and *P. ovale* separately or simultaneously using the primer sets, can be applied more rapidly and easily than microscopy, and have sensitivity equivalent to PCR. Therefore, the primer sets and method can be advantageously applied on-site, especially in a malaria endemic area, for the rapid and simple detection and identification diagnosis of the *Plasmodium* genus and species simultaneously, in a large number of samples.

Example 3

According to the present invention, from the test results obtained on-site (in a clinic) in a malaria endemic area in a short period of time, mefloquine and artesunate can be prescribed for administration to the five patients diagnosed and identified as being infected with *P. falciparum* in Example 2, based on the information about malaria therapeutic agents and the priority thereof in the malaria therapeutic agent information stored in the "treatment guide database". Likewise, chloroquine and primaquine can be prescribed for administration to the 13 patients diagnosed and identified as being infected with *P. vivax*. Thus, an anti-malaria measure support system can be operated which is capable, in a malaria endemic area, of rapidly and reliably detecting the presence or absence of infection with *Plasmodium* parasites and providing malaria treatment.

Example 4

As described above, simple and easy detection of the genus *Plasmodium* (in particular, the presence or absence of mixed infection) is important in malaria endemic areas.

The present inventors conducted further research on primers that are capable of detecting *Plasmodium* species.

As a result, the inventors found that two types of primer sets (Pv-7 and Pv-9; Pv-7 is represented by SEQ ID NOs: 37 to 42 and Pv-9 is represented by SEQ ID NOs: 31 to 36) that are useful for *P. vivax* diagnosis enable more rapid diagnosis of *P. vivax*.

When using the two types of primer sets, it was demonstrated that these primer sets react none of the DNAs of *P. falciparum*, *P. malariae*, and *P. ovale*.

The use of the two types of primer sets (Pv-7 and Pv-9) useful for *P. vivax* diagnosis achieved more rapid diagnosis (Pv-7: 27 minutes; Pv-9: 24 minutes) than the previously found primer set for *P. vivax* diagnosis (31 minutes). In particular, the use of the primer set Pv-9 achieved the most rapid diagnosis.

The invention further provides the following inventions:

1A. A primer set for detecting the genus *Plasmodium*, comprising an oligonucleotide set containing nucleic acid sequences represented by SEQ ID NOs: 1 to 6, the primer set being capable of amplifying a particular region of a *Plasmodium* 18S rRNA gene sequence.

2A. A primer set for detecting *Plasmodium vivax*, comprising an oligonucleotide set containing nucleic acid sequences represented by SEQ ID NOs: 13 to 18, the primer set being capable of amplifying a particular region of a *Plasmodium vivax* 18S rRNA gene sequence.

3A. A primer set for detecting *Plasmodium malariae*, comprising an oligonucleotide set containing nucleic acid sequences represented by SEQ ID NOs: 19 to 24, the primer set being capable of amplifying a particular region of a *Plasmodium malariae* 18S rRNA gene sequence.

4A. A primer set for detecting *Plasmodium ovale*, comprising an oligonucleotide set containing nucleic acid sequences represented by SEQ ID NOs: 25 to 30, the primer set being capable of detecting a particular region of a *Plasmodium ovale* 18S rRNA gene sequence.

5A. A primer set for detecting the genus *Plasmodium*, *P. falciparum*, *P. vivax*, *P. malariae* or *P. ovale*, comprising an oligonucleotide primer set containing any of the nucleic acid sequences of claims 1A to 4A and nucleic acid sequences represented by SEQ ID NOs: 7 to 12, the primer set being capable of amplifying particular regions of a 18S rRNA gene of the genus *Plasmodium* and various species of *Plasmodium* including a particular region of a *Plasmodium falciparum* 18S rRNA gene sequence.

6A. A method for detecting the genus *Plasmodium* present in a specimen, wherein the method targets a particular region of the genus *Plasmodium* 18S rRNA gene sequence, and comprises selectively amplifying the particular region of the genus *Plasmodium* 18S rRNA gene sequence by LAMP using a primer set of claim 1A, and confirming the presence or absence of an amplified product.

7A. A method for detecting *Plasmodium vivax* present in a specimen, wherein the method targets a particular region of a *Plasmodium vivax* 18S rRNA gene sequence, and comprises selectively amplifying the particular region of the *Plasmodium vivax* 18S rRNA gene sequence by LAMP using a primer set of claim 2A, and confirming the presence or absence of an amplified product.

8A. A method for detecting *Plasmodium malariae* present in a specimen, wherein the method targets a particular region of a *Plasmodium malariae* 18S rRNA gene sequence, and comprises amplifying the particular region of the *Plasmodium malariae* 18S rRNA gene sequence by LAMP using a primer set of claim 3A, and confirming the presence or absence of an amplified product.

9A. A method for detecting *Plasmodium ovale* present in a specimen, wherein the method targets a particular region of a *Plasmodium ovale* 18S rRNA gene sequence, and comprises selectively amplifying the particular region of the *Plasmodium ovale* 18S rRNA gene sequence by LAMP using a primer set of claim 4A, and confirming the presence or absence of an amplified product.

10A. A method for detecting the genus *Plasmodium*, *Plasmodium falciparum*, *Plasmodium vivax*, *Plasmodium malariae*, or *Plasmodium ovale* present in a specimen, wherein the method targets a particular region of the genus *Plasmodium* 18S rRNA gene sequence, the genus *Plasmodium falciparum* 18S rRNA gene sequence, a *Plasmodium vivax* 18S rRNA gene sequence, a *Plasmodium malariae* 18S rRNA gene sequence, or a *Plasmodium ovale* 18S rRNA gene sequence;

and wherein the method comprises selectively amplifying the particular region of the genus *Plasmodium* 18S rRNA gene sequence, *P. falciparum* 18S rRNA gene sequence, *P. vivax* 18S rRNA gene sequence, *P. malariae* 18S rRNA gene sequence, or *P. ovale* 18S rRNA gene sequence respectively; by LAMP using a primer set of claim 5A; and confirming the presence or absence of an amplified product.

11A. A detection method according to claim 10A, wherein the genus *Plasmodium*, *P. falciparum*, *P. vivax*, *P. malariae* or *P. ovale* are detected simultaneously or separately.

12A. A method for identifying the genus *Plasmodium*, comprising isolating a DNA sample from a specimen, performing LAMP amplification of a particular region of the genus *Plasmodium* 18S rRNA gene sequence from the DNA sample using a primer set of claim 1A, and confirming the presence or absence of an amplified product.

13A. A method for identifying *Plasmodium vivax*, comprising isolating a DNA sample from a specimen, performing LAMP amplification of a particular region of a *Plasmodium vivax* 18S rRNA gene sequence from the DNA sample using a primer set of claim 2A, and confirming the presence or absence of an amplified product.

14A. A method for identifying *Plasmodium malariae*, comprising isolating a DNA sample from a specimen, performing LAMP amplification of a particular region of a *P. malariae* 18S rRNA gene sequence from the DNA sample using a primer set of claim 3A, and confirming the presence or absence of an amplified product.

15A. A method for identifying *Plasmodium ovale*, comprising isolating a DNA sample from a specimen, performing LAMP amplification of a particular region of a *P. ovale* 18S rRNA gene sequence from the DNA sample using a primer set of claim 4A, and confirming the presence or absence of an amplified product.

16A. A method for identifying the genus *Plasmodium, P. falciparum, P. vivax, P. malariae*, or *P. ovale*, comprising isolating a DNA sample from a specimen, performing LAMP amplification of a particular region of the genus *Plasmodium* 18S rRNA gene sequences, a *P. falciparum* 18S rRNA gene sequence, a *P. vivax* 18S rRNA gene sequence, a *P. malariae* 18S rRNA gene sequence, or a *P. ovale* 18S rRNA gene sequence, from the DNA sample using a primer set of claim 5A; and confirming the presence or absence of an amplified product.

17A. A method of identification according to claim 16A, wherein the identification of any of the genus *Plasmodium, P. falciparum, P. vivax, P. malariae*, or *P. ovale* is performed simultaneously or separately.

18A. A detection kit for the genus *Plasmodium, P. falciparum, P. vivax; P. malariae*, or *P. ovale;* comprising at least a primer set of any of claim 1A to 5A, a strand displacement DNA polymerase, dNTPs and a reaction buffer.

19A. A detection kit according to claim 18A, wherein the detection kit detects the genus *Plasmodium, P. falciparum, P. vivax, P. malariae*, or *P. ovale*, simultaneously or separately.

20A. An anti-malaria measure support system comprising:
means for inputting and storing malaria-infected patient information including the number positive for the genus *Plasmodium* parasites that cause malaria in a malaria endemic area, and the carrier rate in the area;
a malaria infection-prevention public health measure guide database that specifies public health measures for the malaria endemic area based on the malaria-infected patient information, into which database public health measure selection information for a malaria parasite-infected area to be inputted together with the measure priority indicating which of the public health measures should be given priority in selection has been inputted;
a public health measure extraction section that extracts public health measures for the malaria-infected endemic area and the priority thereof from the malaria infection-prevention public health measure guide database, according to malaria-infected patient information about malaria parasites in a subject; and
a public health measure display section that displays the public health measures extracted in the public health measure extraction section, together with the priority thereof.

21A. An anti-malaria measure support system according to claim 20A, wherein the malaria-infected patient information about malaria parasites in the malaria endemic area is obtained by identifying the presence or absence of infection with the genus *Plasmodium* using a primer set according to claim 1A and/or a detection method according to claim 6A, or the genus *Plasmodium* detection kit according to claim 19A.

22A. An anti-malaria measure support system comprising:
means for inputting and storing malaria therapeutic agent information for specifying a malaria therapeutic agent that acts on infection with one or a plurality of four species of malaria parasites;
patient information input means for inputting and storing patient information including information about the pathogen of malaria infection in a patient with a fever in a malaria endemic area;
patient information input means for inputting and storing patient information including information about the pathogen of malaria infection in a patient with a fever in a malaria non-endemic area;
a treatment guide database into which, according to indices of efficacy against malaria parasites detected in a subject, malaria therapeutic agent selection information to be inputted together with a priority that indicates which malaria therapeutic agent should be given priority in selection for use against the malaria parasites;
a malaria therapeutic agent extraction section that extracts, according to the information about the pathogen of malaria infection in the subject, malaria therapeutic agents to be administered and the priority thereof, from the treatment guide database; and
a malaria therapeutic agent display section that displays the malaria therapeutic agents extracted in the above malaria therapeutic agent extraction section, together with the priority thereof.

23A. An anti-malaria measure support system according to claim 22A, wherein the information about the pathogen of malaria infection in a patient with a fever is obtained by identifying infection with one or a plurality of four species of malaria parasites using a primer set according to any one of claims 2A to 5A and/or a method for identifying the genus *Plasmodium, Plasmodium falciparum, Plasmodium vivax, Plasmodium malariae*, or *Plasmodium ovale* according to any one of claims 13A to 17A, or a detection kit according to claim 18A or 19A.

24A. An anti-malaria measure support system in which a public health measure relating to an anti-malaria measure and a malaria parasite treatment measure relating to an anti-malaria measure are carried out in combination;
the public health measure comprising:
means for inputting and storing malaria-infected patient information including the number positive for the genus *Plasmodium* that causes malaria in a malaria endemic area, and the carrier rate in the area;
a malaria infection-prevention public health measure guide database that specifies public health measures for the malaria endemic area based on the malaria-infected patient information, into which database public health measure selection information for a malaria parasite-infected area to be inputted together with a priority of measures that indicates which of the public health measures should be given priority in selection has been inputted;
a public health measure extraction section that extracts public health measures for the malaria-infected endemic area and the priority thereof, from the malaria infection-prevention public health measure guide database according to malaria-infected patient information about malaria parasites in the subject; and
a public health measure display section that displays the public health measures extracted in the public health measure extraction section, together with the priority thereof; and the malaria parasite treatment measure comprising:

means for inputting and storing malaria therapeutic agent information for specifying a malaria therapeutic agent that acts on infection with one or a plurality of four species of malaria parasites;

patient information input means for inputting and storing patient information including information about the pathogen of malaria infection in a patient with a fever in the malaria endemic area;

patient information input means for inputting and storing patient information including information about the pathogen of malaria infection in a patient with a fever in a malaria non-endemic area;

a treatment guide database into which, according to indices of efficacy against malaria parasites detected in a specimen, malaria therapeutic agent selection information to be inputted together with a priority that indicates which malaria therapeutic agent should be given priority in selection for use against the malaria parasites;

a malaria therapeutic agent extraction section that extracts, according to the information about the pathogen of malaria infection in the subject, malaria therapeutic agents to be administered and the priority thereof, from the treatment guide database; and a malaria therapeutic agent display section that displays the malaria therapeutic agents extracted in the above malaria therapeutic agent extraction section, together with the priority thereof.

25A. An anti-malaria measure support system according to claim 24A, wherein the malaria-infected patient information about malaria parasites in the malaria endemic area is obtained by identifying the presence or absence of infection with the genus *Plasmodium* using a primer set according to claim 1A and/or a detection method according to claim 6A, or the genus *Plasmodium* detection kit according to claim 19A; and/or information about the pathogen of malaria infection in a patient with a fever is obtained by identifying infection with one or a plurality of four species of malaria parasites using a primer set according to any one of claims 2A to 5A and/or a method for identifying the genus *Plasmodium*, *Plasmodium falciparum*, *Plasmodium vivax*, *Plasmodium malariae*, or *Plasmodium ovale* according to any one of claims 13A to 17A, or a detection kit according to claim 18A or 19A.

26A. A malaria infection-prevention measure system for persons who plan to travel to a malaria endemic area, the system comprising:

means for obtaining the state of the implementation of public health measures in the malaria endemic area, information about the pathogens of malaria infection in the endemic area, and the state of the treatment of infected patients, from the anti-malaria measure support system according to claim 24A;

means for selecting a malaria prophylactic/therapeutic agent from a malaria parasite treatment guide database; and means for administering the selected agent before travel.

27A. A malaria infection-prevention/treatment measure system for returnees from a malaria endemic area, the system comprising:

means for obtaining the state of the implementation of public health measures in the malaria endemic area, information about the pathogens of malaria infection in the endemic area, and the state of the treatment of infected patients;

means for selecting a malaria prophylactic/therapeutic agent from a malaria parasite treatment guide database; and means for administering the selected agent after returning from the malaria endemic area, according to Item 24.

28A. A malaria infection-prevention/treatment measure system according to claim 27A, wherein, when a returnee from the malaria endemic area has a fever, identification of *Plasmodium falciparum*, *Plasmodium vivax*, *Plasmodium malariae*, or *Plasmodium ovale* is performed to select and administer a malaria therapeutic agent that should be given priority in selection.

Industrial Applicability

The method for detecting/identifying the genus *Plasmodium* and four species of malaria parasites using LAMP developed by the present inventors have higher sensitivity and higher specificity than microscopy, and can detect/identify the *Plasmodium* parasites in specimens more easily and in a shorter period of time than PCR. Further, since the method is inexpensive, it is very useful for malaria clinical diagnosis and control activity in malaria endemic areas with poor facilities. It is also possible to construct a new anti-malaria measure support system (FIG. 3) using the method.

Sequence Listing Free Text

The 18S rRNA sequences of four *Plasmodium species*, *P. falciparum* (GenBank Accession No. M19172), *P. vivax* (GenBank Accession No. U03079 or X13926), *P. malariae* (GenBank Accession No. M54897), and *P. ovale* (GenBank Accession No. L48987), were aligned for comparison.

The invention claimed is:

1. A primer set for detecting *Plasmodium malariae*, comprising the oligonucleotides of SEQ ID NOs: 19 to 24, the primer set being capable of amplifying a particular region of the *Plasmodium malariae* 18S rRNA gene.

* * * * *

UNITED STATES PATENT AND TRADEMARK OFFICE
CERTIFICATE OF CORRECTION

| | | |
|---|---|---|
| PATENT NO. | : 9,222,140 B2 | Page 1 of 1 |
| APPLICATION NO. | : 14/571888 | |
| DATED | : December 29, 2015 | |
| INVENTOR(S) | : Takafumi Tsuboi and Eun-Taek Han | |

It is certified that error appears in the above-identified patent and that said Letters Patent is hereby corrected as shown below:

On the Title Page,

"(72) Inventors: Takafumi Tsuboi, Matsuyama (JP);
                Eun-Taek Han, Chuncheon (JP)" should be -- (72) Inventors: Takafumi Tsuboi, Matsuyama (JP);
               Eun-Taek Han, Chuncheon (KR) --.

Signed and Sealed this
Twelfth Day of April, 2016

Michelle K. Lee
*Director of the United States Patent and Trademark Office*